(12) United States Patent
Curti et al.

(10) Patent No.: US 7,832,400 B2
(45) Date of Patent: *Nov. 16, 2010

(54) NASAL AND ORAL CANNULA HAVING TWO CAPABILITIES AND METHOD OF PRODUCING SAME

(75) Inventors: James N. Curti, Bakersfield, CA (US); Peter W. Salter, Bakersfield, CA (US)

(73) Assignee: Salter Labs, Arvin, CA (US)

( * ) Notice: Subject to any disclaimer, the term of this patent is extended or adjusted under 35 U.S.C. 154(b) by 1032 days.

This patent is subject to a terminal disclaimer.

(21) Appl. No.: 11/011,012

(22) Filed: Dec. 13, 2004

(65) Prior Publication Data

US 2005/0103347 A1     May 19, 2005

Related U.S. Application Data

(60) Continuation-in-part of application No. 10/265,527, filed on Oct. 4, 2002, now Pat. No. 6,830,445, which is a division of application No. 09/883,843, filed on Jun. 18, 2001, now Pat. No. 6,533,984, which is a continuation-in-part of application No. 09/754,471, filed on Jan. 4, 2001, now Pat. No. 6,533,983.

(51) Int. Cl.
*A61M 15/08* (2006.01)
*A61M 16/00* (2006.01)

(52) U.S. Cl. .............. 128/207.18; 128/204.22; 128/200.24; 128/204.18; 128/203.22; 128/206.21

(58) Field of Classification Search ............ 128/207.18, 128/205.27, 205.28, 203.22, 200.24, 203.12, 128/203.18

See application file for complete search history.

(56) References Cited

U.S. PATENT DOCUMENTS

| 2,053,357 | A | 9/1936 | Winder |
| 2,296,011 | A | 9/1942 | Beal |
| 2,824,407 | A | 2/1958 | Ebel |

(Continued)

FOREIGN PATENT DOCUMENTS

EP     0 993 094 A2     4/2000

(Continued)

OTHER PUBLICATIONS

Salter Labs, "Dual Oral/Nasal ETCO 2 Sampling Cannulas", Copyright 1991, Revised Sep. 2003.

*Primary Examiner*—Justine R Yu
*Assistant Examiner*—Clinton Ostrup
(74) *Attorney, Agent, or Firm*—Davis & Bujold, P.L.L.C.

(57) ABSTRACT

A nasal cannula comprising a hollow main body having opposed first and second openings formed therein and the main body defining an internal chamber. A partition divides the internal chamber into first and second flow compartments. A flow passageway of a first nasal prong communicates with the first compartment and a flow passageway of the first mouth piece communicates with the first compartment to define a first flow passageway which communicates with both a first nostril and a mouth of the patient. A flow passageway of a second nasal prong communicates with the second compartment and a flow passageway of the second mouth piece communicates with the first compartment to define a second flow passageway which communicates with both a second nostril and the mouth of the patient.

14 Claims, 15 Drawing Sheets

U.S. PATENT DOCUMENTS

| | | |
|---|---|---|
| 2,854,695 A | 10/1958 | Moreau |
| 3,643,660 A | 2/1972 | Hudson et al. |
| 3,731,900 A | 5/1973 | Havstad |
| 3,802,431 A | 4/1974 | Farr |
| 3,906,071 A | 9/1975 | Cook et al. |
| 3,931,381 A | 1/1976 | Lindberg |
| 4,106,505 A | 8/1978 | Salter et al. |
| 4,152,688 A | 5/1979 | Dietz |
| 4,433,219 A | 2/1984 | Dietz |
| 4,602,643 A | 7/1986 | Dietz |
| 4,695,241 A | 9/1987 | Ventimiglia |
| 4,745,925 A | 5/1988 | Dietz |
| 4,800,116 A | 1/1989 | Ventimiglia et al. |
| 4,818,320 A | 4/1989 | Weichselbaum |
| 4,878,502 A | 11/1989 | Dietz |
| 5,005,571 A | 4/1991 | Dietz |
| 5,024,219 A | 6/1991 | Dietz |
| 5,038,771 A | 8/1991 | Dietz |
| 5,046,491 A | 9/1991 | Derrick |
| 5,052,400 A | 10/1991 | Dietz |
| 5,074,299 A | 12/1991 | Dietz |
| 5,133,923 A | 7/1992 | Klug |
| 5,335,656 A | 8/1994 | Bowe et al. |
| 5,380,182 A | 1/1995 | Packard et al. |
| 5,485,833 A | 1/1996 | Dietz |
| 5,485,850 A | 1/1996 | Dietz |
| 5,513,634 A | 5/1996 | Jackson |
| 5,682,881 A | 11/1997 | Winthrop et al. |
| 5,922,365 A | 7/1999 | Reichner |
| 6,019,100 A * | 2/2000 | Alving et al. .......... 128/203.12 |
| 6,045,514 A | 4/2000 | Raviv et al. |
| 6,171,258 B1 | 1/2001 | Karakasoglu et al. |
| 6,213,955 B1 | 4/2001 | Karakasoglu et al. |
| 6,217,818 B1 | 4/2001 | Collette et al. |
| 6,247,470 B1 | 6/2001 | Ketchedjian |
| 6,379,312 B2 | 4/2002 | O'Toole |
| 6,422,240 B1 * | 7/2002 | Levitsky et al. ........ 128/207.18 |
| 6,635,214 B2 | 10/2003 | Rapacki et al. |
| 6,830,445 B2 * | 12/2004 | Curti .......................... 425/275 |
| 7,337,780 B2 * | 3/2008 | Curti et al. ............. 128/207.18 |
| 2001/0031929 A1 | 10/2001 | O'Toole |
| 2002/0171175 A1 | 11/2002 | Ainsworth et al. |
| 2005/0051176 A1* | 3/2005 | Riggins ................. 128/207.18 |
| 2005/0103347 A1 | 5/2005 | Curti et al. |
| 2005/0284484 A1* | 12/2005 | Curti et al. ............. 128/207.18 |
| 2006/0174886 A1* | 8/2006 | Curti et al. ............. 128/206.11 |
| 2006/0283463 A1* | 12/2006 | Curti et al. ............. 128/207.18 |

FOREIGN PATENT DOCUMENTS

| | | |
|---|---|---|
| FR | 2 197 613 | 3/1975 |
| JP | 3-500496 | 2/1991 |
| JP | 7-37730 | 7/1995 |
| RU | 1775957 C | 9/1995 |
| RU | 1793628 C | 10/1995 |
| WO | 89/09565 | 10/1989 |
| WO | WO 9848876 A1 * | 11/1998 |

* cited by examiner

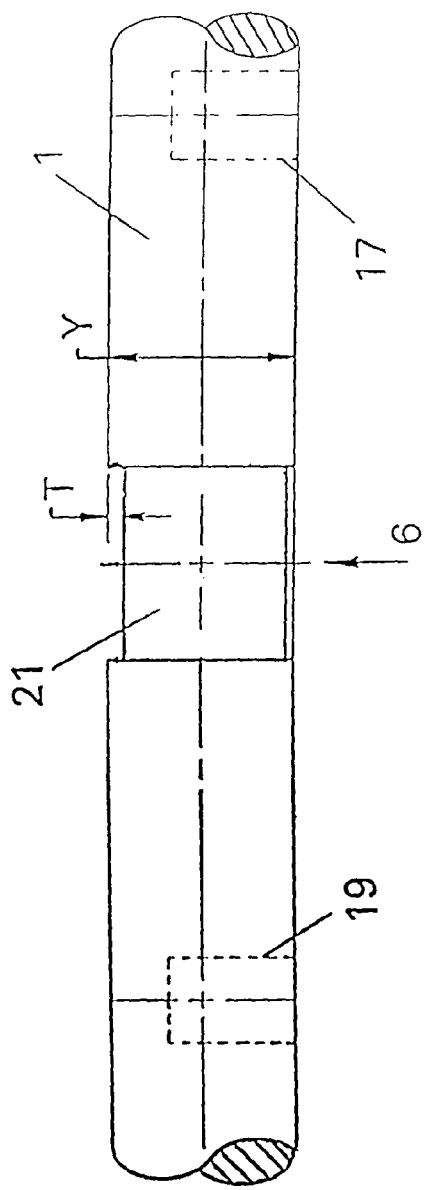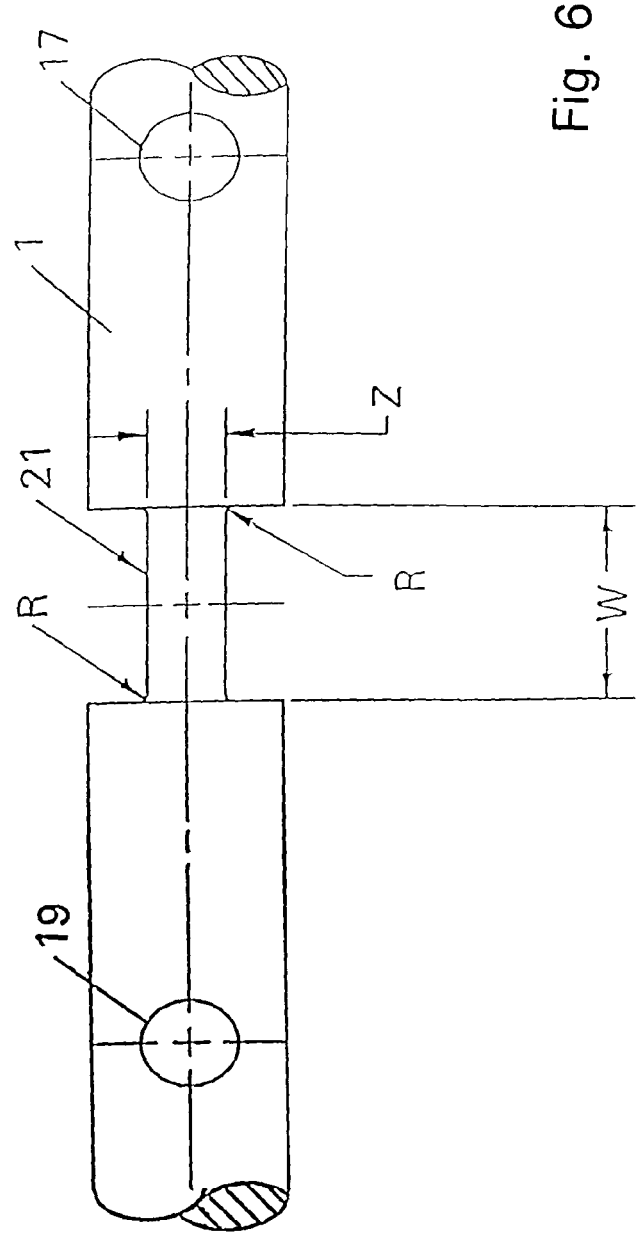

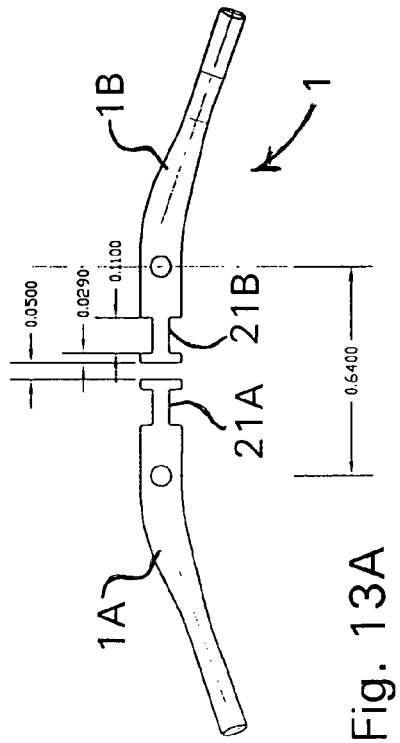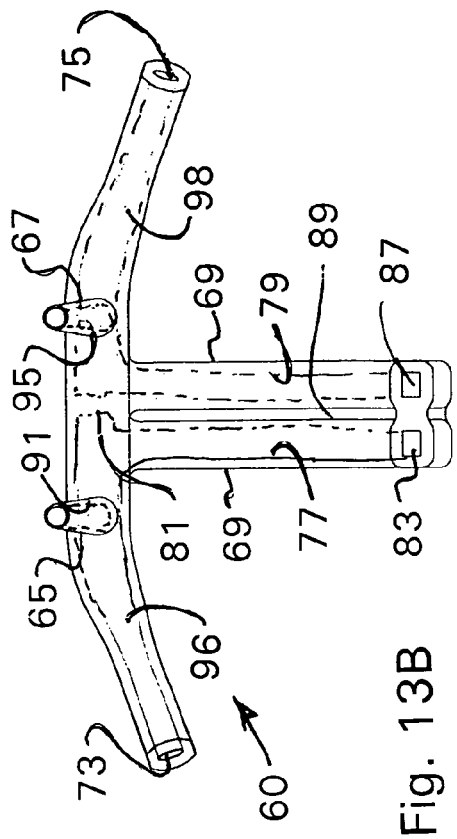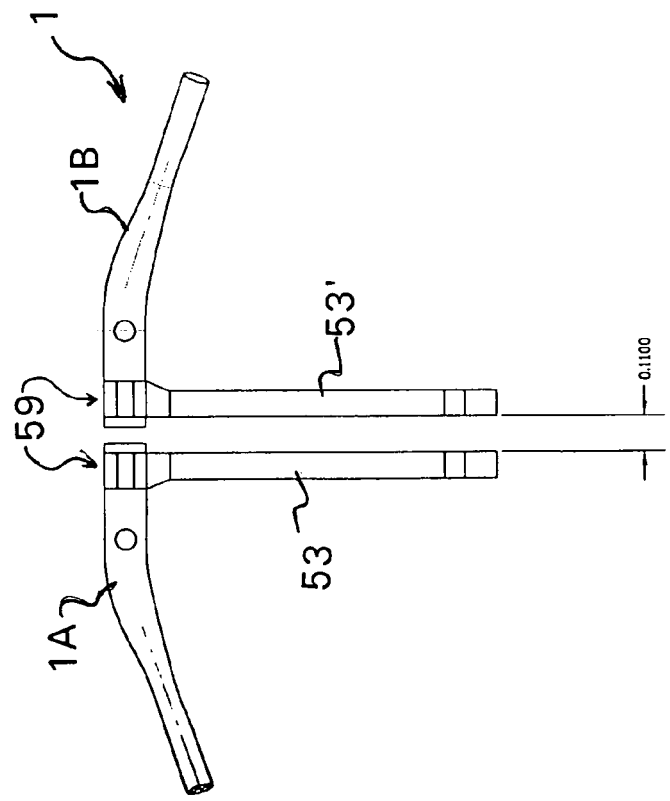
Fig. 13A
Fig. 13B
Fig. 13

NASAL AND ORAL CANNULA HAVING TWO CAPABILITIES AND METHOD OF PRODUCING SAME

This application is a continuation-in-part application of Ser. No. 10/265,527 filed Oct. 4, 2002, now U.S. Pat. No. 6,830,445, which is a divisional of application Ser. No. 09/883,843 filed Jun. 18, 2001, now U.S. Pat. No. 6,533,984, which is a continuation-in-part of application Ser. No. 09/754,471 filed on Jan. 4, 2001, now U.S. Pat. No. 6,533,983 B2.

FIELD OF THE INVENTION

This invention relates to a novel cannula which is suitable for use for both nasal and oral applications and a method of producing the cannula using disconnectable mandrel parts to form a mold over or on which the cannula forming plastics material is applied to form the cannula.

BACKGROUND OF THE INVENTION

This invention relates generally to cannulas adapted for both oral and nasal applications for monitoring breathing of a patient, sampling the end tidal $CO_2$ content in the exhaled breath of a patient to determine the patient's $CO_2$ blood concentration level, or supplying a treating gas, such as oxygen, to a patient. In addition, the invention relates to a method of manufacturing a cannula adapted to communicate with both nasal passages and the mouth of a patient for use in monitoring breathing, sampling end tidal $CO_2$ supplying a treating gas and is also suitable for the detection of apnea (the absence of breathing).

Nasal cannulas are commonly used to administer a treating gas, such as oxygen, to humans having respiratory problems. Illustrations of nasal cannulas used for this purpose are found in U.S. Pat. No. 3,802,431. Nasal cannulas have also been used for inhalation therapy, made possible by development of inhalation sensors, such as described in U.S. Pat. No. 4,745,925. A nasal cannula can be used to monitor breathing and for detection of apnea when connected to an inhalation sensor.

Nasal cannulas additionally adapted to communicate with the mouth of a patient to permit administration of a gas or sensing of apnea during periods of mouth breathing or nasal blockage are also known.

The present invention relates to a novel cannula and method of manufacturing the novel cannula having the ability to communicate with both nasal cavities as well as the mouth or oral cavity of a patient. This apparatus and method provides, in the preferred embodiment, disconnectable mandrel components which, when assembled, form a mold over which a cannula forming polymeric material is applied, and which, through the capability of each mandrel component being disconnectable from the other mandrel component(s), facilitates removal of the mandrel components from the formed or manufactured cannula.

Prior art relating to dipping of a part in a plastisol to create a coating is exemplified by U.S. Pat. Nos. 3,906,071, 4,695,241 and 4,800,116, and the disclosures of those references are hereby incorporated by reference.

The closest known prior art is believed to be a sampling cannula sold under the Salter Labs "One-No. 4001 oral/nasal $CO_2$ sample line" trade designation. This cannula has a pair of prongs or sampling line(s) which each communicate with one nostril of the patient and a pair of straight prongs or sampling line(s) which both communicate with the oral or mouth cavity of the patient. A U-shaped wired is glued or otherwise affixed to the exterior surface of the main body of the cannula but the wire extends only about half the length of each of the oral or mouth cavity prongs or sampling line(s). All of the nasal and the oral and mouth prongs or sampling line(s) communicate with one another so that the cannula can only perform one function. The leading free end of the oral or mouth prongs or sampling line(s) can be bent over in front of the teeth of the patient and any excess length of the prong(s) or sampling line(s) can be trimmed.

SUMMARY OF THE INVENTION

It is an object of the invention to provide a method of manufacturing a cannula using an assembly of disconnectable mandrel components over which cannula forming plastics or polymeric material is applied. Application of the plastics or polymeric material over the mandrel assembly and subsequent extraction of the mandrel components from one another, following sufficient curing of the plastics or polymeric material, results in a manufactured cannula with contiguous internal flow paths for sampling the exhaled breath of a patient to detect the end tidal $CO_2$ in the blood of a patient, sensing patient breathing, and/or supplying a treating gas to the patient.

It is a further object of the invention to provide a multi-part mandrel assembly for forming a cannula which facilitates extraction of each of the mandrel assembly components following at least partial curing of the polymeric material forming the cannula.

Still another object of the invention is to form the main body forming mandrel component as two separate, slightly spaced apart components which remain spaced apart from one another by a gap or void, during the dipping process, so that the gap void becomes filled with a plastics or polymeric material to form a wall, septum or barrier which partitions or divides the internal passage of the cannula into two separate compartments or passageways, one which facilitates either sensing of patient breathing, monitoring of the end tidal $CO_2$ in a patient's blood stream or supplying a treating gas to the patient, etc., while the other of which also facilitates another function, such as, sensing of patient breathing, monitoring of the end tidal $CO_2$ in a patient's blood stream, and/or supplying a treating gas to the patient, etc.

Another object of the invention is to produce a cannula having at least one mouthpiece, and alternatively a pair of side by side mouthpieces, extending from the main body of the cannula to the patient's mouth, the cannula is provided with at least one passageway, or alternatively a pair of passageways, for supplying a gas to the patient via a demand regulator for example, or sampling a patient's oral exhalation for monitoring the end tidal $CO_2$ in a patient's blood stream for instance, and the at least one mouthpiece, or alternatively the pair of mouthpieces, has a desired curvature or orientation so that the opening of each mouthpiece is located in or adjacent the mouth or oral cavity of a patient for detecting or sensing the exhaled breath of the patient.

It is a further object of the invention to provide a nasal cannula which is continuously able to both supply and withdraw a gas sample from a mouth of a breathing patient or a patient which alternates breathing between the nose and the mouth and is also able to continuously detect breathing of a patient who alternates breathing between the nose and the mouth.

Yet another object of the invention to provide a nasal cannula which is relatively inexpensive to manufacture by a dipping process as an integral unitary cannula.

Still another object of the invention is to provide a multi-part mandrel assembly for forming a cannula which facilitates extraction of each of the mandrel assembly components following at least partial curing the polymeric material forming the cannula.

The invention also relates to a nasal cannula comprising: a hollow main body having opposed first and second ends with a first opening formed in the first end and a second opening formed in the second end, and the main body defining an internal chamber therein; a partition dividing the internal chamber into first and second flow compartments, the first flow compartment communicating with the first opening and the second flow compartment communicating with the second opening; a flow passageway of a first nasal prong communicating with the first compartment and a flow passageway of the first mouth piece communicating with the first compartment to define a first flow path communicating with both a first nostril and a mouth of the patient; and a flow passageway of a second nasal prong communicating with the second compartment and a flow passageway of the second mouth piece communicating with the first compartment to define a second flow path communicating with both a second nostril and the mouth of the patient.

The invention also relates to a method of using a nasal cannula comprising a hollow main body having opposed first and second ends with a first opening formed in the first end and a second opening formed in the second end, and the main body defining an internal chamber therein; a partition dividing the internal chamber into first and second flow compartments, the first flow compartment communicating with the first opening and the second flow compartment communicating with the second opening; a flow passageway of a first nasal prong communicating with the first compartment and a flow passageway of the first mouth piece communicating with the first compartment to define a first flow path communicating with both a first nostril and a mouth of the patient; and a flow passageway of a second nasal prong communicating with the second compartment and a flow passageway of the second mouth piece communicating with the first compartment to define a second flow path communicating with both a second nostril and the mouth of the patient, and a first end of a first tubing being connected to the first opening and a first end of a second tubing being connected to the second opening; the method comprising the steps of: placing the first and second nasal prongs in the nostrils of the patient; connecting the second end of the first tubing to one of a device for monitoring breathing of a patient, a device for sampling the end tidal $CO_2$ content in the exhaled breath of a patient to determine the patient's $CO_2$ blood concentration level, a device for supplying a treating gas to the patient and a device for detection of apnea; and connecting the second end of the second tubing to one of a device for monitoring breathing of a patient, a device for sampling the end tidal $CO_2$ content in the exhaled breath of a patient to determine the patient's $CO_2$ blood concentration level, a device for supplying a treating gas to the patient and a device for detection of apnea.

The invention further relates to a method of manufacturing a nasal cannula comprising: a hollow main body having opposed first and second ends with a first opening formed in the first end and a second opening formed in the second end, and the main body defining an internal chamber therein; a partition dividing the internal chamber into first and second flow compartments, the first flow compartment communicating with the first opening and the second flow compartment communicating with the second opening; a flow passageway of a first nasal prong communicating with the first compartment and a flow passageway of the first mouth piece communicating with the first compartment to define a first flow path communicating with both a first nostril and a mouth of the patient; and a flow passageway of a second nasal prong communicating with the second compartment and a flow passageway of the second mouth piece communicating with the first compartment to define a second flow path communicating with both a second nostril and the mouth of the patient, the method comprising the steps of: assemblying a main body mandrel with a pair of nasal mandrels and a pair of oral mandrels; dipping the mandrel assembly in a plastisol to form the nasal cannula on the mandrel assembly; and removing the main body mandrel, the pair of nasal mandrels and the pair of oral mandrels to thereby result in the nasal cannula.

BRIEF DESCRIPTION OF THE DRAWINGS

The invention will now be described, byway of example, with reference to the accompanying drawings, in which:

FIG. 5 is a fragmentary side elevation of the main body mandrel of FIGS. 1 and 2 taken along section line 5-5 of FIG. 2;

FIG. 6 is an elevation of the main body mandrel taken in the direction of arrow 6 in FIG. 5;

FIG. 13 a front elevational view of a further embodiment showing a partially assembled mandrel assembly having the pair of mouthpiece mandrels assembled with the pair of sections of the main body mandrel;

FIG. 13A a front elevational view of only the pair of sections of the main body mandrel;

FIG. 13B is a diagrammatic orthogonal view of a cannula, manufactured from the mandrel assembly of FIG. 13A, having a pair of separate mouthpieces and two separate flow passageways;

DETAILED DESCRIPTION OF THE EMBODIMENTS

Figure 1:
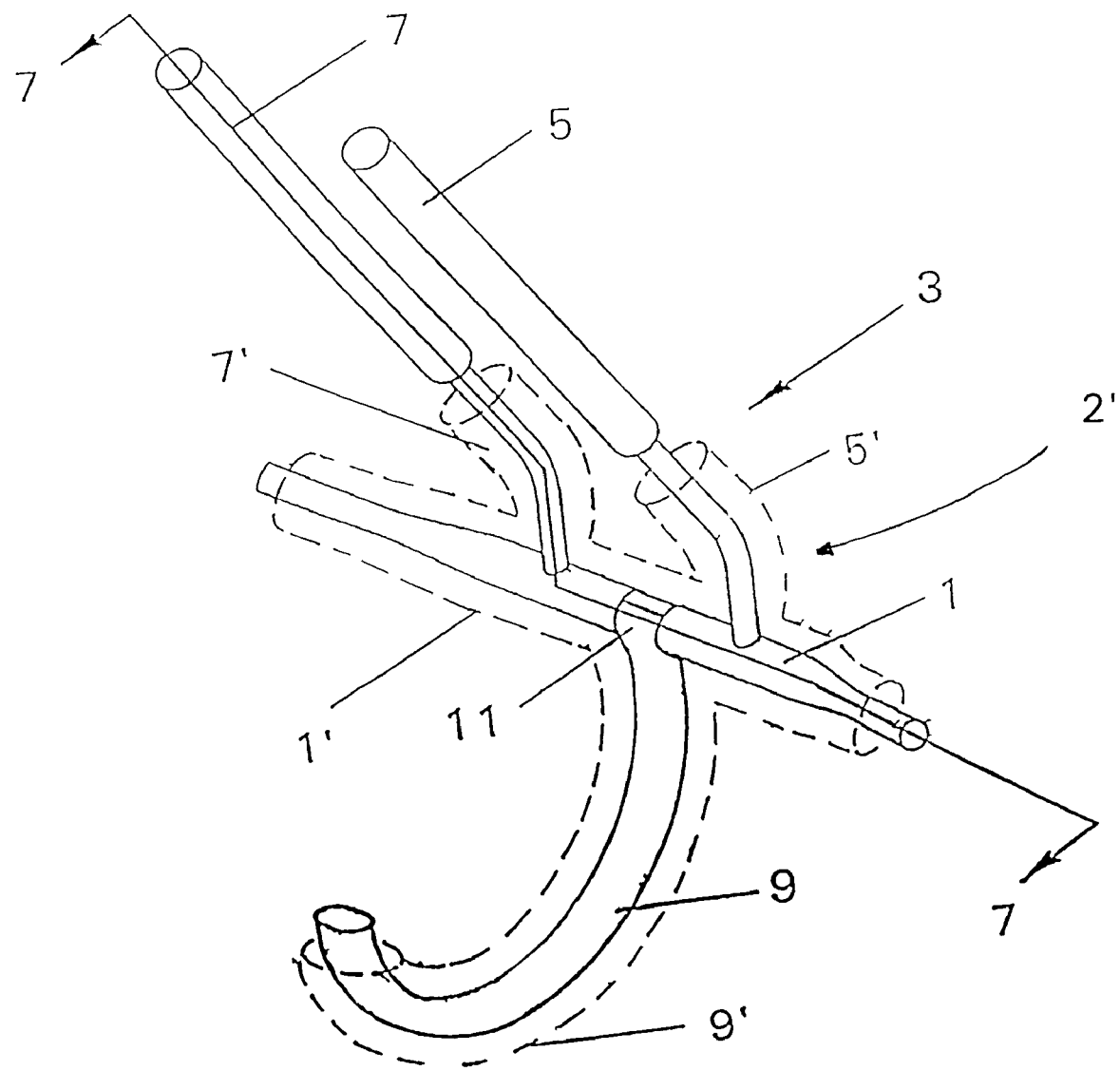
FIG. 1 is an orthogonal view of a cannula mandrel assembly with cannula forming plastics or polymeric material shown in ghost.

Referring to FIG. 1, the main body forming mandrel 1 of a beryllium copper cannula mandrel assembly 3 is shown with a pair of spaced apart nare forming mandrels 5 and 7, and a separate mouthpiece forming mandrel 9 having an end connector 11 for joining the mouthpiece mandrel 9 to the main body forming mandrel 1. A cannula 2', to be formed on the assembly, is shown in ghost and such cannula generally comprises a main body 1', a pair of nares 5', 7' and a mouthpiece 9' composed of polyvinyl chloride (PVC), for example.

Figure 2:
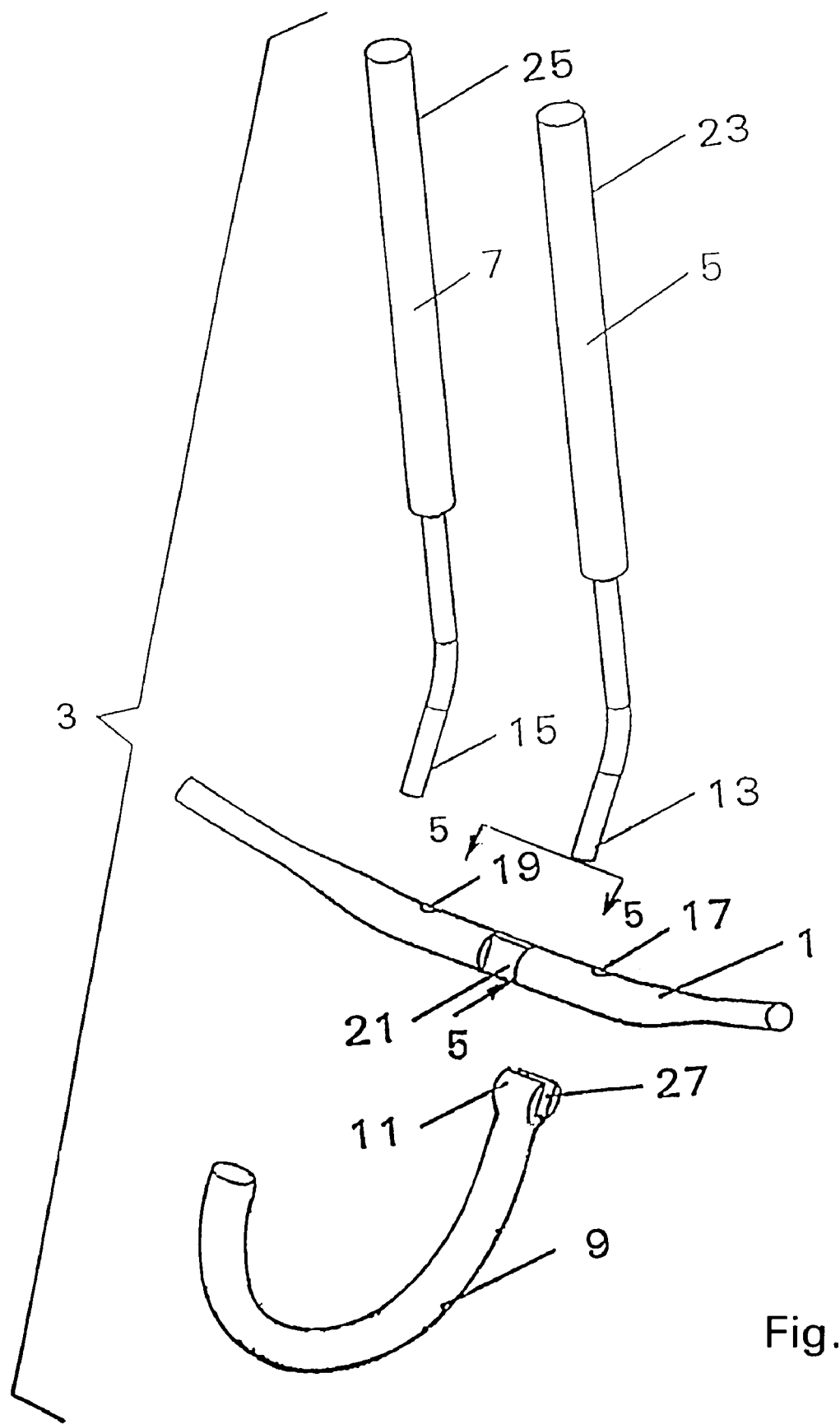
FIG. 2 is an orthogonal view of the cannula mandrel parts prior to assembly.

FIG. 2 shows the mandrel assembly components prior to assembly in order to form or produce the cannula mandrel assembly 3. Each of the nare mandrels 5 and 7 has a reduced diameter section 13 or 15 which form nares 5', 7', respectively, over which cannula forming plastics or polymeric material is applied. Reduced diameter sections 13 and 15 of nare mandrels 5 and 7 matingly slide into and are received by respective blind holes 17 and 19 of main body mandrel 1 (see FIG. 5). Main body mandrel 1 also has a central rectangular recessed section 21 which slidably mates and receives the end connector 11 of mouthpiece mandrel 9.

Nare mandrels 5 and 7 also have enlarged diameter sections 23 and 25 which facilitate support a plurality of identical cannula mandrel assemblies 3 in a jig (not shown) during the molding process. Additionally, the enlarged diameter enables sections 23 and 25 provide a larger contact surface which allows easier gripping of nare mandrels 5 and 7 to facilitate removal of the nare mandrels 5 and 7 from main body mandrel 1 after partial curing of the PVC, or some other plastisol or plastics material, on the cannula mandrel assembly 3.

FIG. 2 further shows the mouthpiece mandrel 9 with the end connector 11 which has a centrally located slot 27 (see FIG. 3) which slidably engages with the rectangular section 21 of the main body mandrel 1. Slot 27 is sized to permit close contact or engagement of the slot 27 with the rectangular section 21 of main body mandrel 1 such that a snug fit or attachment is obtained so as to removably retain the mouthpiece mandrel 9 on the main body mandrel 1 while also facilitating extraction of the mouthpiece mandrel 9 from the rectangular section 21 following partial curing of the PVC, or some other plastisol or plastics material, on the cannula mandrel assembly 3. The outer surface of end connector 11 is sized to approximate a continuation of the outer surface or diameter of main body mandrel 1 to provide a substantially uniform amount of applied PVC, or some other plastisol or plastics material, to the cannula mandrel assembly 3 and still facilitate withdrawal of the mouthpiece mandrel 9 from the cannula mandrel assembly 3 and the mouthpiece 9' of the cannula.

Figure 3:
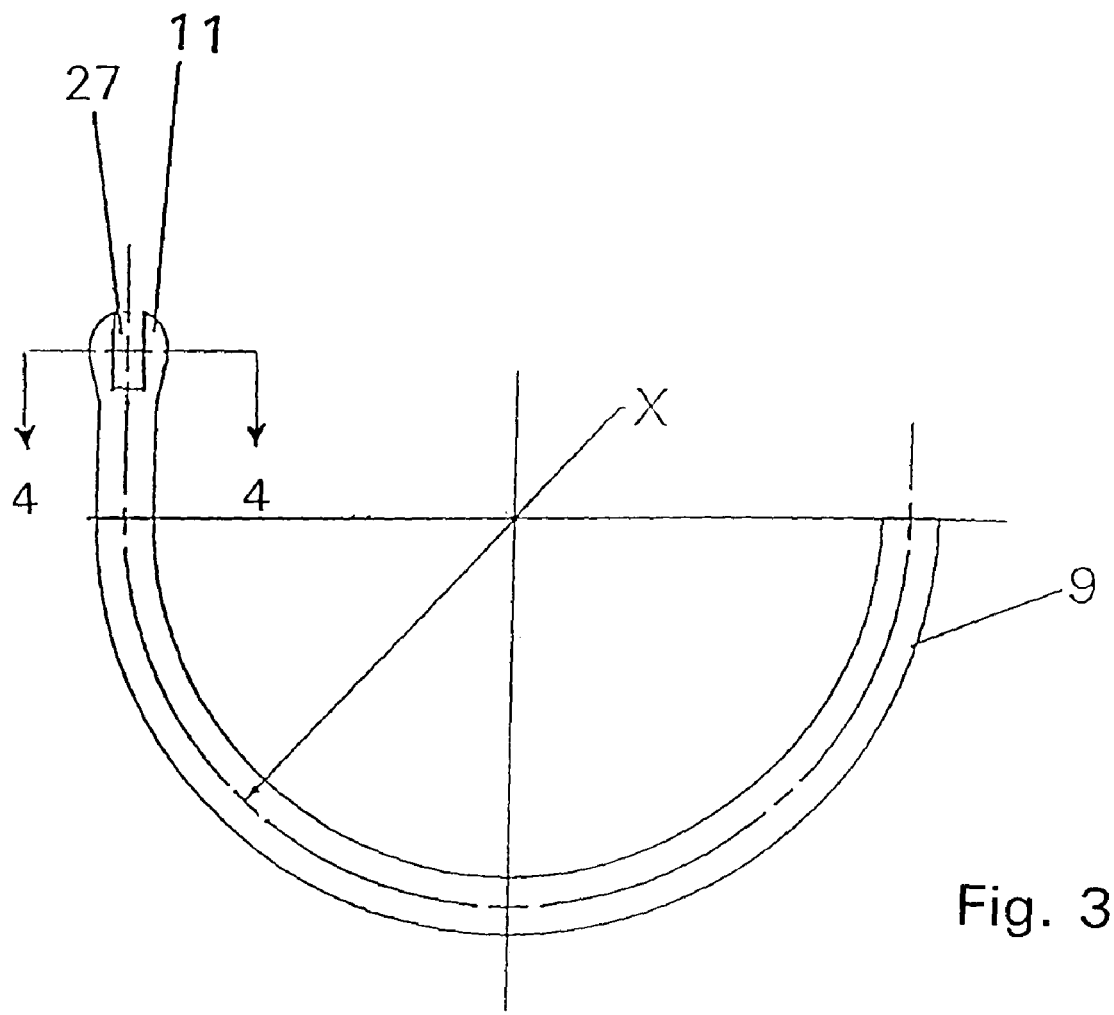
FIG. 3 is a side elevation of the mouthpiece mandrel of FIGS. 1 and 2 showing an end connector.

FIG. 3 shows the general contour of the mouthpiece mandrel 9 having a desired radius X with the end connector 11 located at one end of the mouthpiece mandrel 9 and having a slot 27 formed in the end connector 11.

Figure 4:
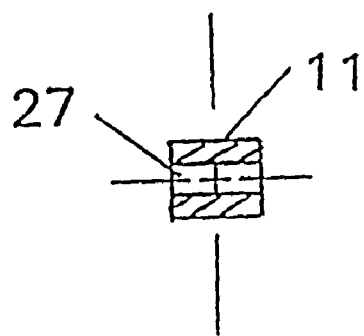
FIG. 4 is an end section of the end connector taken along section line 44 of FIG. 3.

FIG. 4 is a view along section line 4-4 of FIG. 3 which shows the shape, e.g., the length, the width, and the thickness, of the end connector 11 and the slot 27.

Referring to FIGS. 5 and 6, a pair of spaced apart blind holes 17 and 19 are formed in a central region of the main body mandrel 1. Each blind hole 17 and 19 is sized to matingly receive, via a sliding fit, one of the reduced diameter sections 13 or 15 of the nare mandrels 5 and 7 in order to engage and support nare mandrels 5 and 7 in a proper molding orientation during application of the PVC, or some other plastisol or plastics material, to the cannula mandrel assembly 3 for formation of the cannula 2'. The rectangular section 21 is made with a shoulder depth T removed to allow the diameter of end connector 11 of mouthpiece mandrel 9 to mate approximately flush with the diameter Y of main body 1.

The rectangular section 21 is shown preferably with a relieving radii R at opposed ends of the section. The relief radius R may be omitted if the main body mandrel 1 is machined or formed in a manner that allows this. Thickness Z of rectangular section 21 permits slot 27 of end connector 11 of mouthpiece mandrel 9 to firmly but slidably mate with rectangular section 21 and adequately maintain the engagement between those two components with one another during dipping. Width W of rectangular section 21 is just sufficient to closely accommodate end connector 11 of mouthpiece mandrel 9, e.g., a very small clearance fit between those two components is provided.

FIGS. 1 and 2 show nare mandrels 5 and 7 with bend sections 12 and 14. These bend sections 12 and 14 sufficiently curve or direct the nares of the cannula 2', following manufacture of the cannula, so that the nares may be properly aligned to be received within a patient's nasal cavities.

Although beryllium copper is the preferred material for manufacture of the cannula mandrel assembly 3, other materials which possess appropriate working temperature ranges, retain dimensional stability for reuse in a manufacturing environment and will easily and readily release the cannula 2' following partial curing of the PVC, or some other plastisol or plastics material, may be used. Metals including, but not limited to, steel, aluminum, bronze, brass, and copper alloys may be used, as well as some plastics materials. Beryllium copper is preferred due to its ability to transfer heat rapidly and reliably release the cured PVC, plastisol or other plastics material formed on the cannula mandrel assembly 3. Rapid heat transfer is desirable for the material forming the mandrel assembly both during heating of the cannula mandrel assembly 3 and following application of the cannula forming plastics or polymeric material where a partial cure of the plastics or polymeric material is followed by rapid cooling.

Prior to application of a plastics or polymeric solution, such as PVC, the cannula mandrel 3 is coated, usually by dipping step or process, with a silicone release layer or agent to facilitate separation and/or removal of the mandrel components from the plastics or polymeric material to be applied. The application of the plastics or polymeric material, in the preferred embodiment, is by dipping the silicone coated cannula mandrel assembly 3 which has been heated in an oven at an oven temperature of from about 350° F. to about 550° F. (preferably about 450° F.) for about 1 to about 3 minutes prior to dipping in a plastisol solution of PVC. One or more dipping steps may be performed to achieve the desired finished cannula material thickness and each of these dipping steps may be for a duration of 10-30 seconds, for example. During dipping, the mandrel is supported by the outer free enlarged sections 23 and 25 of the nare mandrels.

The use of a plastisol solution, such as PVC, provides a semi-clear finished cannula with sufficient strength to withstand subsequent attachment of various connectors while still being sufficiently flexibility to prevent injury or irritations to the user. Alternatively, other plastics or polymeric materials, which have material properties suitable for this method, capable of forming a plastisol, may be substituted for PVC.

Partial curing of the cannula takes place on the mandrel assembly 3. The cannula mandrel assembly with the partially cured PVC thereon is then placed in an oven, for a sufficient time, for further curing at a temperature from about 410° F. to about 450° F. Following curing to stabilize the PVC and after the cannula has sufficiently cooled, the mandrel components are then removed from the manufactured cannula and the release layer or agent assists with such removal, without damaging the cannula. The resulting manufactured nasal cannula has sufficient physical strength and retains its manufactured configuration.

Using the inventive method, a cannula with two nares and a mouthpiece is formed as follows: a cannula mandrel assembly 3 is formed by first, slidably mating reduced diameter sections 13 and 15 of nare mandrels 5 and 7 into the blind holes 17 and 19, respectively, of the main body mandrel 1; second, orienting nare mandrels 5 and 7 so that they are properly aligned as shown in FIG. 1; third, slidably mating the slot 27 of the end connector 11 of the mouthpiece mandrel 9 with the rectangular section 21 of the main body mandrel 1 in a desired orientation relative to the nare mandrels 5 and 7 so that it is also properly aligned as shown in FIG. 1; fourth, supporting the mandrel assembly in a jig and providing a silicone release layer or agent substantially encompassing the mandrel components; fifth, heating the assembled cannula mandrel assembly in an oven at a temperature of from about 350° F. to about 550° F.; sixth, providing a liquid uncured plastisol solution (PVC); seventh, dipping the cannula mandrel assembly into the liquid uncured plastisol solution (PVC), at least once, until the desired material thickness is built-up and/or achieved on the mandrel assembly 3; eighth, at least partially curing the plastisol (PVC) at a temperature of about 410° F. to about 450° F.; and ninth, following sufficient curing, removing the nare mandrels 5 and 7 from the blind holes 17 and 19 of main body mandrel 1 and the nares 5', 7' by pulling on enlarged diameter sections of the nare mandrels 5 and 7, and removing the mouthpiece mandrel 9 from the mouthpiece 9' by disengaging the slot 27 of the end connector 11 from the rectangular section 21 of the main body mandrel 1 and pulling the mouthpiece mandrel 9 out through the mouthpiece 9'; and finally slidably removing main body mandrel 1 from the main body 1' of the cannula by extracting or withdrawing the same from one end of the manufactured cannula 2'.

Figure 7:
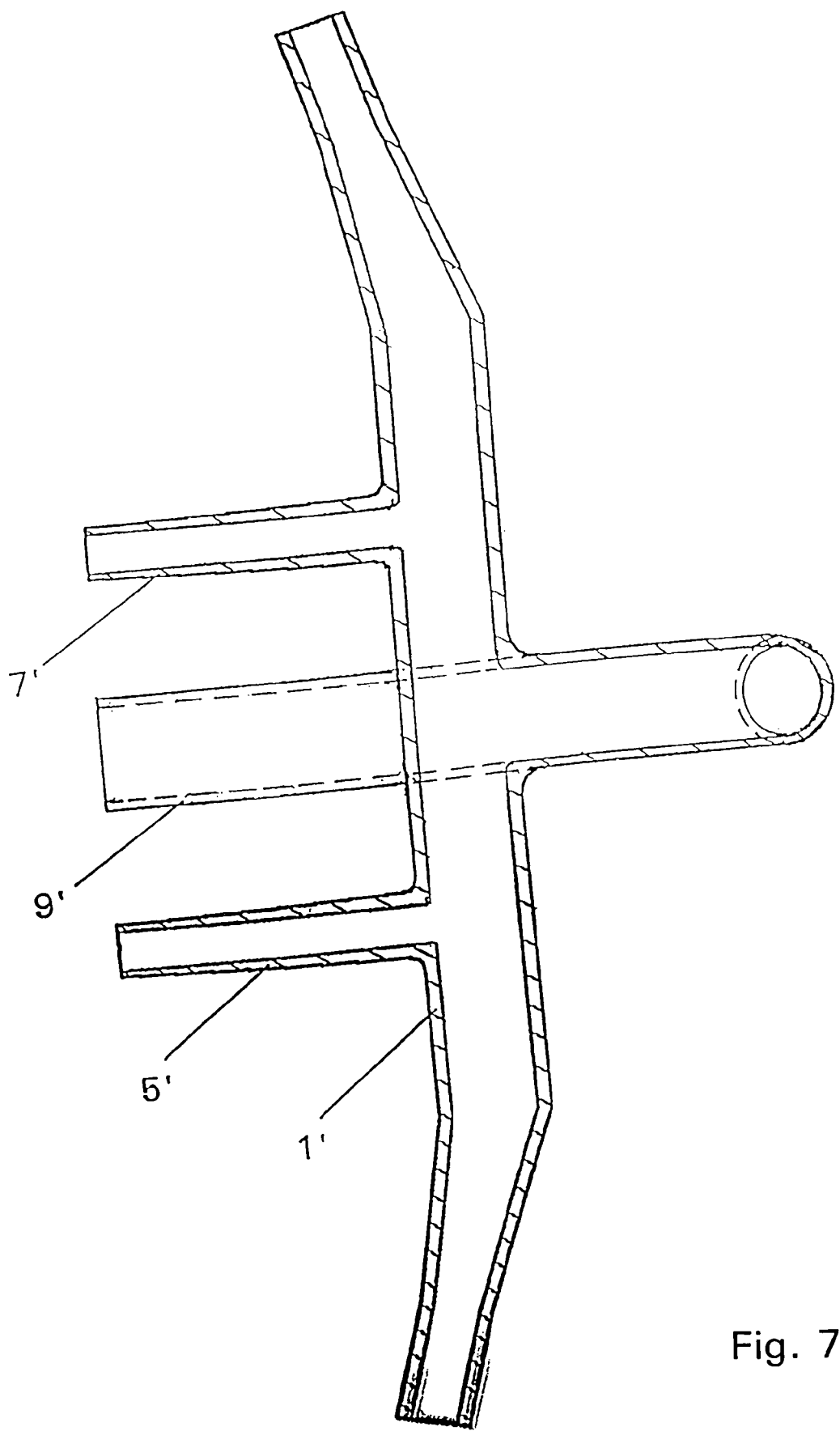
FIG. 7 is a diagrammatic cross-sectional view of a cannula, made by the method of the present invention, taken along section line 7-7 of FIG. 1.
Figure 8:
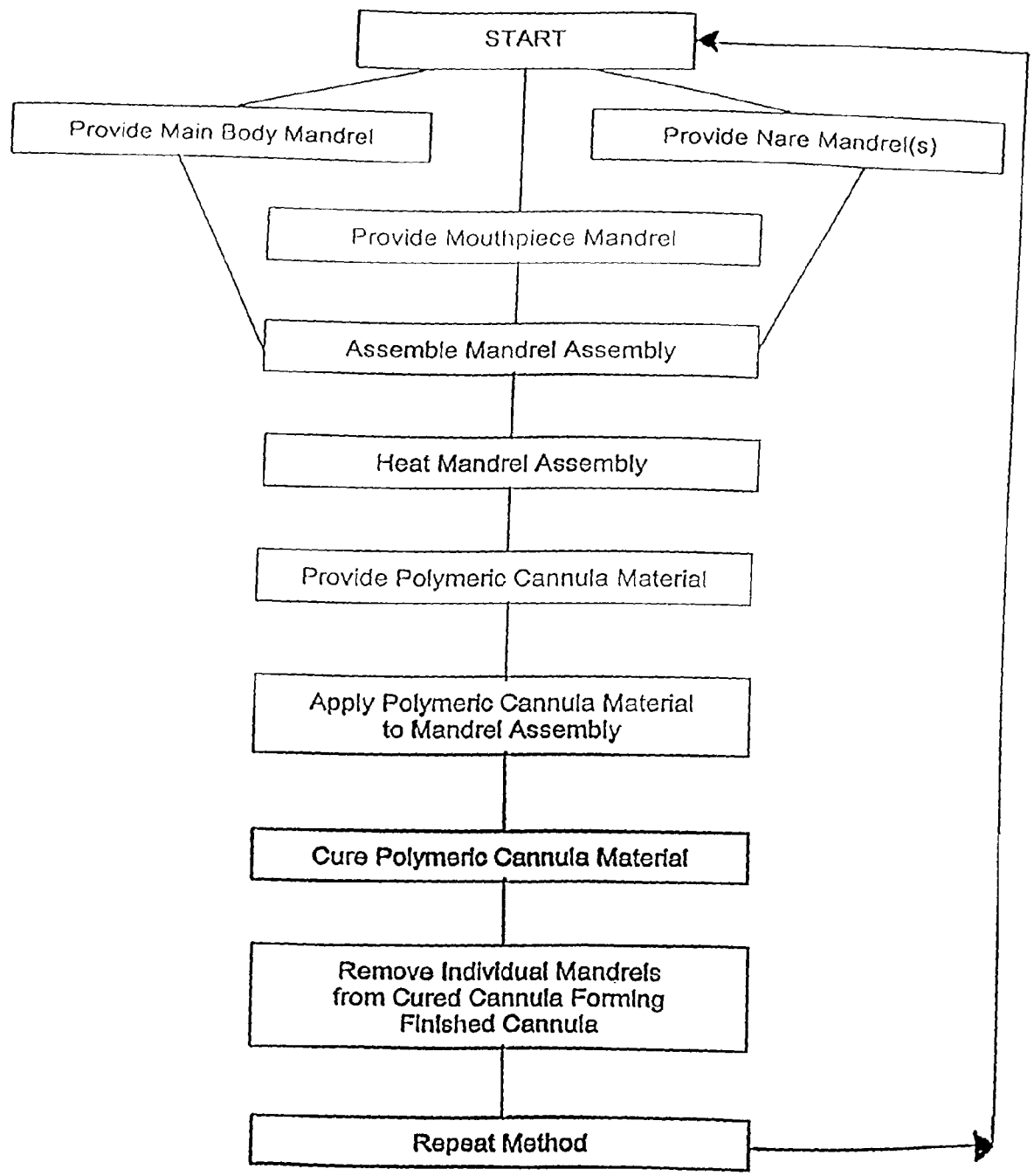
FIG. 8 is a flow diagram of the method of the present invention.
Figure 9:
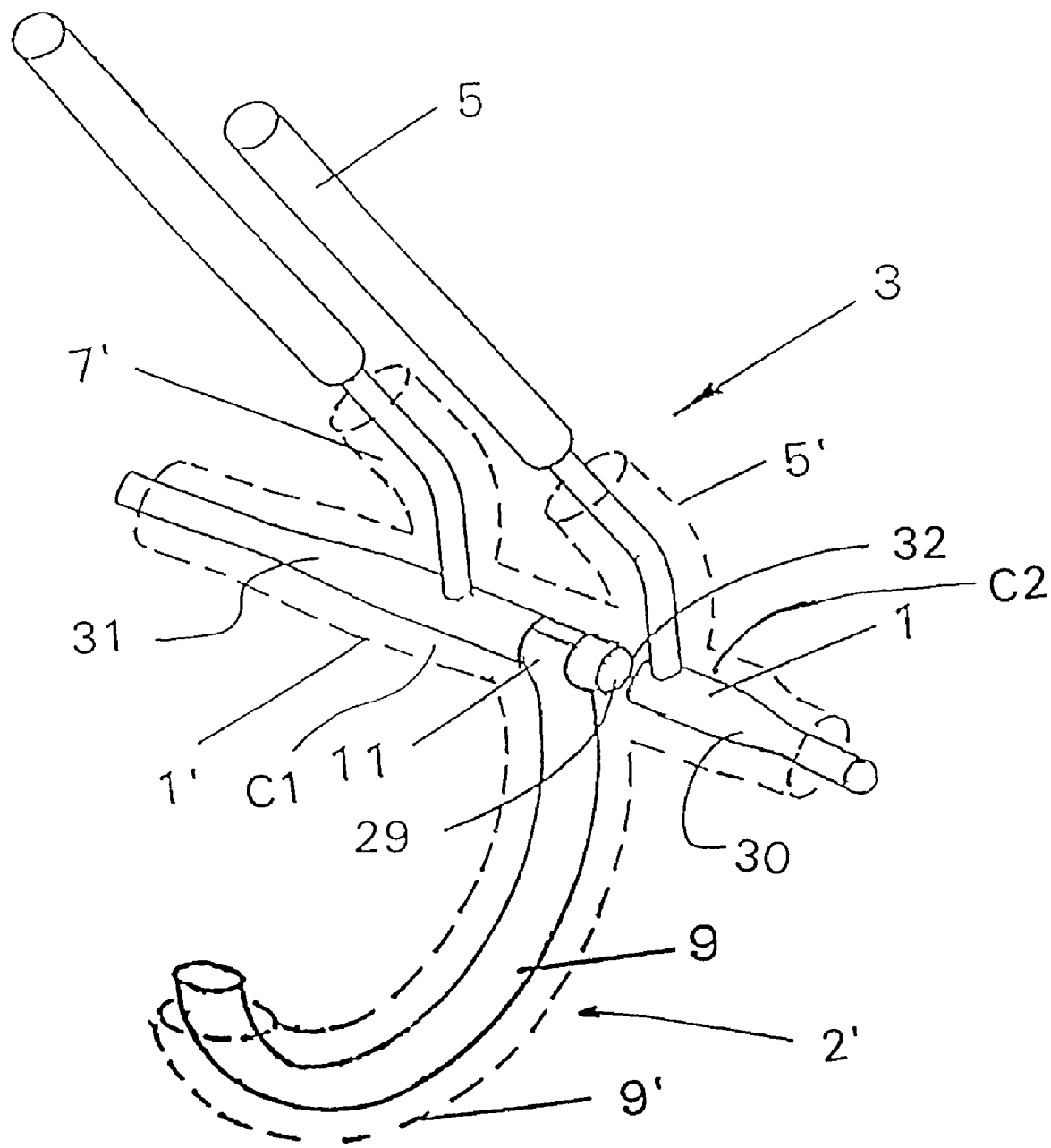
FIG. 9 is an orthogonal view of a cannula mandrel assembly for forming a septum or barrier in a void of the main body forming mandrel, with cannula forming plastics or polymeric material shown in ghost.
Figure 10B:
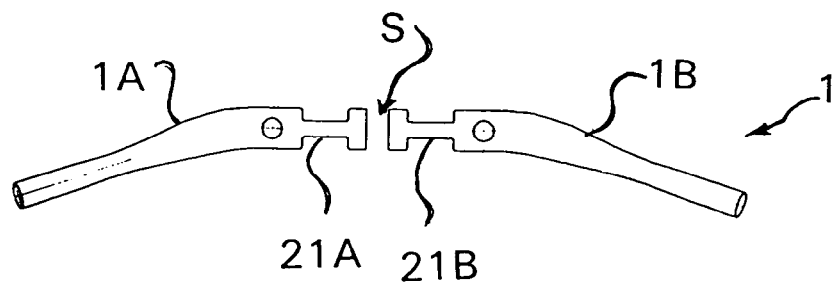
FIG. 10B a front elevational view of only the pair of sections of the main body mandrel.
Figure 10A:
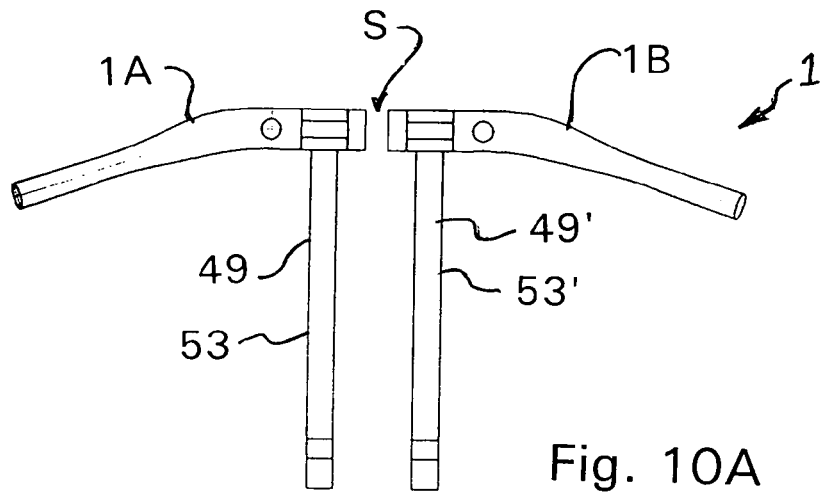
FIG. 10A a front elevational view of another embodiment showing a partially assembled mandrel assembly having the pair of mouthpiece mandrels assembled with the pair of sections of the main body mandrel.
Figure 10C:
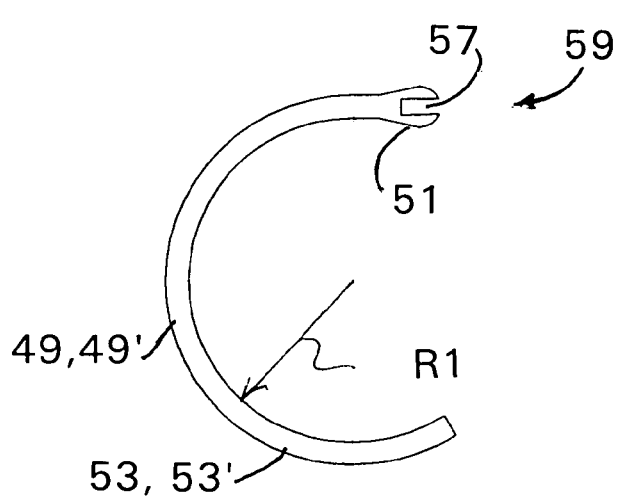
FIG. 10C a side elevational view of one prong for forming the gas flow passageway in the mouthpiece.
Figure 10D:
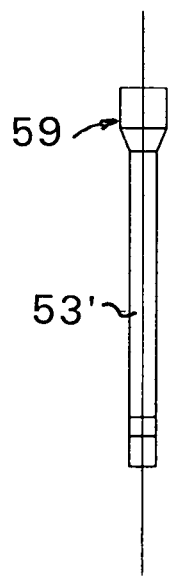
FIG. 10D a front elevational view of the prong of FIG. 10C.

FIG. 7 shows a diagrammatic cross sectional view of a finished or manufactured cannula 2', following removal of the components of the cannula mandrel assembly 3 from the cured PVC cannula, and the formed contiguous flow paths through the main body 1', the nares 5' and 7' and the mouthpiece 9' can be seen.

It will be appreciated that the curing step may be completed in two stages, namely, a first partial cure of the PVC produced by the heated cannula mandrel assembly 3 which is sufficient to maintain the PVC on this assembly and a second stage in an oven at the above indicated curing temperatures to complete curing, following the partial curing of the PVC, the plastisol or some other plastics material.

It will be further appreciated that the opposed outer ends of the main body 1' of the manufactured cannula 2' may be trimmed, as necessary or desired, to provide a discrete area where a flexible connecting tubing or conduit may be connected thereto, e.g., by solvent bonding with MEK (methyl ethyl ketone) for example, and the mouthpiece 9' may be trimmed to a desired length suited to an individual patient so as to maximize the sensitivity of the finished cannula, e.g., sensing patient breathing, monitoring end tidal $CO_2$ in a patient's blood stream or supplying a treating gas to the patient.

It will also be understood that disassembly of the cannula mandrel assembly 3, following curing of the cannula forming polymeric material, can proceed by removing the mouthpiece mandrel before the nare mandrels as an obvious alternative method step, prior to removal of the main body mandrel.

One modification of the present invention relates to the addition or formation of an internal wall or septum in the internal passage of the cannula 2' to provide an internal partition or barrier therein, e.g., form a "divided cannula." The septum 29 divides the internal chamber C of the main body 1' of the cannula 2' into two separate compartments or passageways C1 and C2 so that a first one of the nares 5' can be coupled to a treating gas, such an oxygen source (not shown), to facilitate the supply of supplemental oxygen to one of the nostrils of a patient while the other one of the nares 7' and the central mouthpiece 9' can be coupled to a monitoring device (not shown), such as a transducer, to facilitate monitoring of breathing of the patient or coupled to a demand oxygen conserving device (not shown) while the patient, at the same time, is still able to receive, either continuously or intermittently during the sensed breathing cycle, a supplemental supply of oxygen. Alternatively, one of the nares 5' can be connected to a capnograph, for example, to sample the exhaled breath of a patient and detect the end tidal $CO_2$ in the blood stream of a patient or sensing of patient breathing.

In order to manufacture the septum 29, the main body forming mandrel 1 is formed as first and second separate, slightly spaced apart mandrel components 30, 31 which remain spaced apart from one another by a small gap or void 32 following assembly of the cannula mandrel assembly 3 and during the dipping operation of the manufacturing process so that the void 32 between the first and the second separate, slightly spaced apart mandrel components 30, 31 becomes filled with PVC, or some other plastisol or plastics material, and forms the septum 29. Once the cannula is adequately cured, the septum 29 forms an internal partition or barrier within the main body 1' of the cannula which divides the internal chamber C into two separate compartments or passageways C1 and C2.

Following sufficient curing, the nare mandrels 5 and 7 are removed from the blind holes 17 and 19 of main body mandrel 1 and the nares 5', 7' by pulling on enlarged diameter sections of nare mandrels 5 and 7, the mouthpiece mandrel 9 is removed from the mouthpiece 9' by disengaging the slot 27 of the end connector 11 from the rectangular section 21 of the main body mandrel 1 and pulling the mouthpiece mandrel 9 out through the mouthpiece 9'; and the first and second spaced apart components 30, 31 of the main body mandrel 1 are removed from the main body 1' of the cannula by pulling the first and second spaced apart components 30, 31 axially away from one another and out from the main body 1' of the cannula 2'. As discussed above, the opposed outer ends of the main body 1' of the manufactured cannula 2' may be trimmed, as necessary or desired, to facilitate connection to a connecting tubing or conduit.

This variation of the manufacturing process is suitable for intermittent nocturnal oxygen delivery even though the patient breaths through his or her mouth.

As can be seen in FIGS. 10A-10D and 11, another embodiment of the present invention relates to the cannula mandrel assembly 3 for forming a divided cannula having a pair of spaced apart mouthpieces. For the sake of clarity, the nare mandrels 5 and 7 are not shown attached respectively to the first or the second sections 1A, 1B of the main body forming mandrel 1. The first mouthpiece mandrel 49 comprises a first prong 53 for forming a first gas passageway 77 in the first mouthpiece of the manufactured cannula 60 and the second mouthpiece mandrel 49' comprises a second prong 53' for forming a second gas passageway 79 in the second mouthpiece of the manufactured cannula 60. A further description of the same follows below.

In order to attach both the first and second mouthpiece mandrels 49, 49' to the main body mandrel 1, each of the first and second mouthpiece mandrels 49, 49' include an end connector 51 (see FIG. 10C) attached to a connecting end 59 of the respective first and second prongs 53, 53'. The end connector 51 has a centrally located slot 57 which slidably engages or receives one of the two rectangular sections 21A, 21B (see FIG. 10B) formed in one of the two spaced apart but adjacent body sections 1A, 1B forming the main body mandrel 1, as described above. Each slot 57 is sized to closely contact and engage the respective rectangular section 21A or 21B of main body mandrel 1 of each body section 1A, 1B such that a snug fit and retention of each respective mouthpiece mandrel 49, 49' with the main body mandrel 1 is obtained both prior to and during dipping while still also facilitating extraction of the mouthpiece mandrels 49, 49' from rectangular sections 21A, 21B following partial curing and cooling of the PVC, or some other plastisol or plastics material. As with the other embodiments, the outer surface of end connector 51 has a shape, a size and/or contour which approximates the outer diameter of the main body mandrel 1 to provide a uniform diameter of applied cannula forming polymeric material while also facilitating withdrawal of the mouthpiece mandrels 49, 49' from the mouthpieces 69, 69' of the manufactured cannula 60 (see FIG. 11).

The first and second mouthpiece mandrels 49, 49' once coupled to the main body mandrel 1, extend parallel to but are spaced from one another by a small distance, e.g., 1/16 to 1/2 inch or so, more preferably spaced from one another by a distance of 1/4 of an inch. The first and second prongs 53, 53' each have a cross sectional area of between about 0.006 and about 0.007 square inches and a radius of curvature R1 of between about 0.5 of an inch to about 2.5 inches or so, and more preferably a radius of curvature of between about 0.75 of an inch to about 1.25 inches or so. The radius of curvature R1 can vary but is generally chosen to facilitate the alignment of the cannula mouthpiece with a patient's open mouth. The separation between the first and second prongs 53, 53', according to this embodiment, forms a uniform elongate spacing or area between those to prongs so that a sufficient space is provided during the dipping operation(s), which applies a plastisol coating to the cannula mandrel assembly 3 and each of the first and second prongs 53, 53' without any plastisol interconnecting or joining the two mouthpieces 69, 69' with one another, i.e., the two mouthpieces 69, 69' are completely separate and movable independent of one another following formation of the cannula 60.

The transverse cross sectional area D (see FIG. 11) of the openings 83, 87 and the internal gas flow passageway 77, 79 within the mouthpiece 69, 69' of the cannula, once the first and second prongs 53, 53' are removed therefrom, are sufficiently sized for supplying a desired treating gas to a patient, for example, via a demand regulator to a mouth breathing patient. Alternatively, the respective internal gas flow passageway within the mouthpiece 69, 69' of the cannula is sufficiently sized to allow withdrawal, detection, sampling, etc., of an exhalation gas(es) from a mouth of a breathing patient. It is to be appreciated that the transverse cross sectional area of the internal gas flow passageway, formed in the mouthpiece 69, 69' for supplying a treating gas to a patient, may typically be larger than the transverse cross sectional area of a gas flow passageway for withdrawing or sampling a gas(es) from a patient. But, for the sake of simplicity of manufacture and for added versatility, the transverse cross sectional areas of both formed internal gas flow passageways 77, 79 in the first and second mouthpieces 69, 69' can be manufacture identical to one another.

Figure 11:
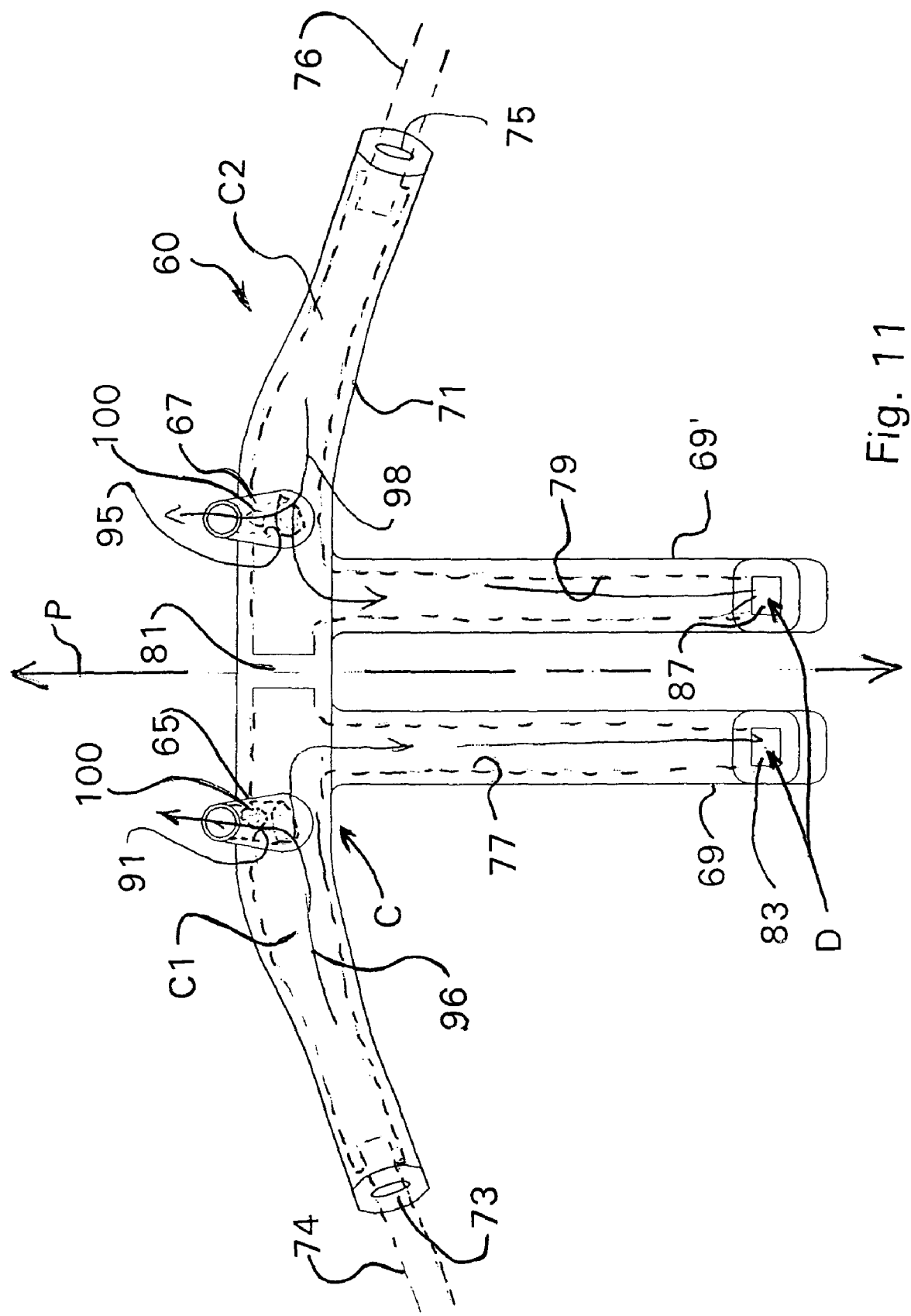
FIG. 11 is a diagrammatic orthogonal view of a cannula, manufactured from the mandrel assembly of FIG. 10, having a pair of separate mouthpieces and two separate flow passageways.

The above described first and second mouthpiece mandrels 49, 49' are each assembled with one of the body sections 1A or 1B of the main body mandrel 1 and one of the first and second nare mandrels 5, 7 to form the cannula mandrel assembly 3. Before dipping, the cannula mandrel assembly 3 is sprayed or otherwise coated with an release film, layer or agent and pre-heated to a desired temperature and then dipped in the cannula forming polymeric plastisol to provide a desired thickness or layer of a partially cured plastics or polymeric material on the exterior surface of the cannula mandrel assembly 3 and thereby form a manufactured plastisol cannula. The partially cured manufactured plastisol cannula is again heated in an oven to further cure the plastics or polymeric material, as previously described. After sufficient curing of the plastics or polymeric material, both of the first and second nare forming mandrels 5, 7, the first and second mouthpiece forming mandrels 49, 49' and the first and second sections 1A, 1B of the main body forming mandrels 1 are extracted from the cured polymeric material and the remaining cured structure results in the manufactured and cured cannula 60, as shown in FIG. 11. I desired or necessary the end of the cannula 60 can be trimmed to a desired length.

The manufactured cannula 60, formed from the above described process and cannula mandrel assembly 3 shown in FIGS. 10A-10D, after addition of the nare mandrels 5 and 7, comprises a main body 71 with a pair of opposed internal chamber end openings 73, 75 located at opposite ends of the main body 71 for coupling, by an adhesive such as MEK for example, each opposed end of the cannula to a flexible gas delivery, pressure detecting or gas sampling tubing or some other conduit 74, 76 (only partially shown in FIG. 11). The gap or spacing formed between the adjacent ends of the first and second sections 1A, 1B of the main body forming mandrel 1 (see FIGS. 10A and 10B) creates a partition, a wall, a dividing member or a septum 81 which divides the internal chamber C into a first compartment or passageway C1 and a completely separate second compartment or passageway C2. The first compartment or passageway C1 communicates with the first chamber end opening 73 while the second separate compartment or passageway C2 communicates with the second chamber end opening 75. A first fluid passageway 91, formed in the first centrally located nasal prong 65, communicates with the first compartment or passageway C1 while a second fluid passageway 95, formed in a second centrally located nasal prong 67, communicates with the second separate compartment or passageway C2. The first gas passageway 77, formed in the first mouthpiece 69, communicates with the first compartment or passageway C1 while the second gas flow passageway 79, formed in the second mouthpiece 69', communicates with the second separate compartment or passageway C2. The pair of centrally located but spaced apart nasal prongs 65, 67 are formed on the cannula for insertion into the nostrils of a patient's nose while the first and second centrally located mouthpieces 69, 69' are formed in the cannula substantially adjacent the middle section of the main body 71, between the nasal prongs 65, 67, for communication with the mouth of the patient.

Figure 11A:
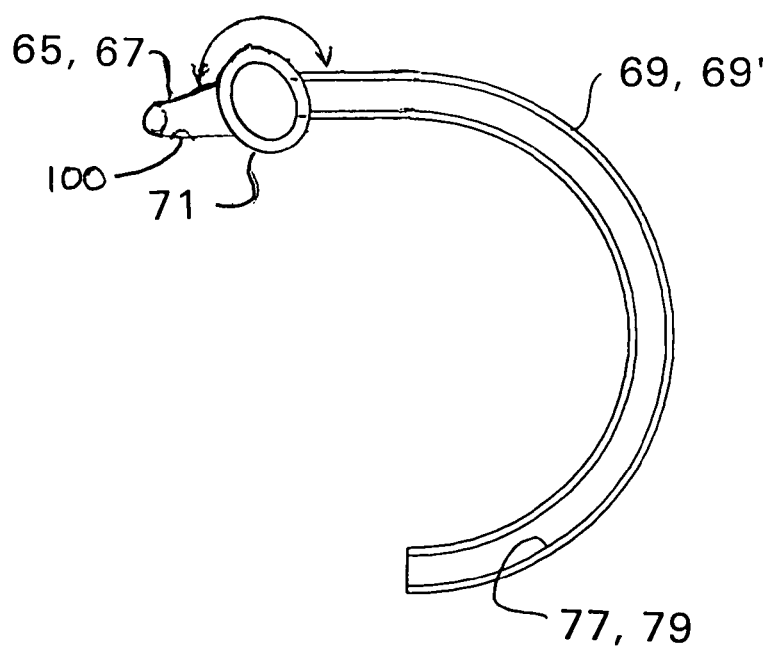
FIG. 11A is a diagrammatic side elevational view of a cannula of FIG. 11.

As best seen in FIG. 11A, the first and second mouthpieces 69, 69' of the nasal cannula 60 are shown in their originally molded shape or configuration which generally corresponds to the curvature of the mouthpiece mandrel 49. As can be appreciated, due to the nature of the resiliency of the plastisol material which forms the cannula 60, the first and second mouthpieces 69, 69' will generally retain and/or return back to such originally molded curvature. As discussed above, the mouthpiece 69, 69' may be trimmed to a desired length (shown in dashed lines in FIG. 12B) to suited an individual patient so as to maximize the sensitivity of the cannula, e.g., sensing patient breathing, monitoring end tidal $CO_2$ in a patient's blood stream, supplying a treating gas to the patient, detecting sleep apnea, etc. That is, the gas passage openings 83 and 87 are generally aligned with, e.g., extends substantially perpendicular to, the exhalation/inhalation path E of the patient.

It is to be appreciated that the nasal cannula 60 is a unitary structure comprising two completely separate internal flow paths 96 and 98. Each one of the two completely separate internal flow paths 96 and 98 is suitable for supplying a treating gas to a patient both via a nostril and the mouth of a patient as well as capable of withdrawing or sampling an exhalation gas(es) from the patient, or monitoring breathing characteristics, detecting pressure, etc. The first compartment or passageway C1, of the internal chamber C of the main body of the cannula 60, is in constant and continuous communication with the first gas passageway 77 of the first mouthpiece 69 and also in constant and continuous communication with the first gas passageway 91 in the first nasal prong 65 and all of these compartments and passageways form the first completely separate internal flow path 96. The second compartment or passageway C2, of the internal chamber C of the main body of the cannula 60, is in constant and continuous communication with the second gas passageway 79 of the second mouthpiece 69' and also in constant and continuous communication with the second gas passageway 95 in the second nasal prong 67 and all of these compartments and passageways form the second completely separate internal flow path 98. As a result of these completely separate fluid passageways 96, 98, each completely separate fluid passageway 96 or 98 can facilitate preforming one of the following functions: monitor breathing of a patient via the mouth and/or the nose, sampling the end tidal $CO_2$ content in the exhaled breath of a patient via the mouth and/or the nose to determine the patient's $CO_2$ concentration level in the blood, supplying a treating gas to a patient via the mouth and/or the nose, detecting apnea via the mouth and/or the nose, etc. If desired, the septum 81 may be eliminated so that the first and second compartments or passageways C1 and C2, the first and second internal gas passageways 77, 79 and the first and second gas passageways 91 and 95 in the nasal prongs 65 and 67 are all in constant and continuous communication with one another.

It is to be appreciated that it is not necessary to have the two mouthpieces 69, 69' precisely centered between the nasal prongs 65, 67. It is conceivable that the mouthpieces could be located on one side or the other of a central plane P bisecting a center of main body 71 into two halves. It is to be appreciated further that it is not necessary to have the septum 81 center within the main body as long as the septum 81 is generally located between the nasal prongs 65, 67. Also, as set forth in U.S. Pat. No. 6,439,234 to Curti et al., the disclosure of which is hereby incorporated by reference, additional openings 100 (shown as dashed lines in FIG. 11), preferably adjacent the remote free end of each nasal prong, could be provided in the nasal prongs 65, 67 and possibly in the gas passageway 69, 69' of the mouthpiece to prevent occlusion of the nasal prongs and facilitate monitoring, detecting, sampling, delivery, etc.

As can be seen in FIG. 11A for example, the first end of the nasal prongs 65 and 67 generally form an angle of between about 180° or so ±5 degrees with the connected end of the mouthpieces 69, 69'.

Figure 12A:
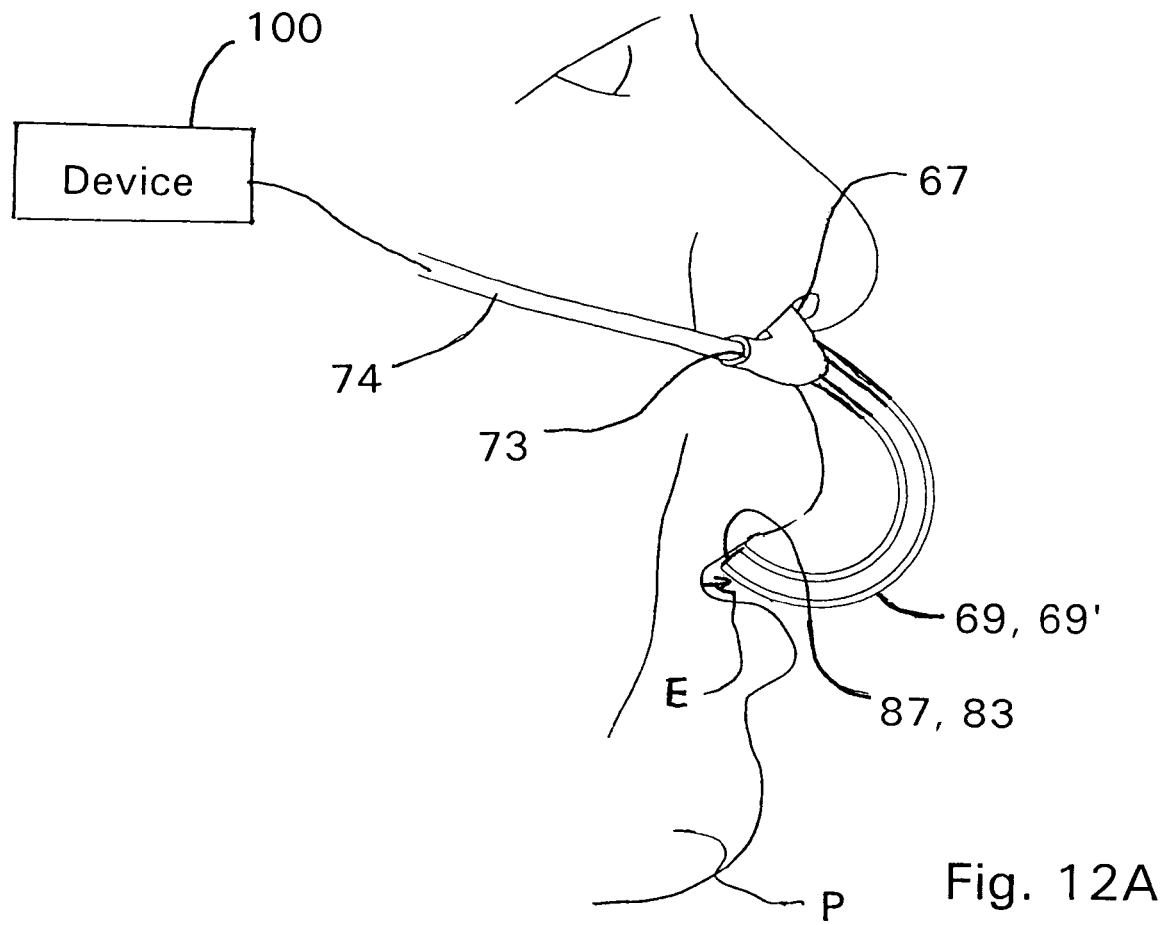
FIG. 12A is a side elevational views showing the originally molded orientation of the mouthpiece relative to an open mouth of a patient.
Figure 12B:
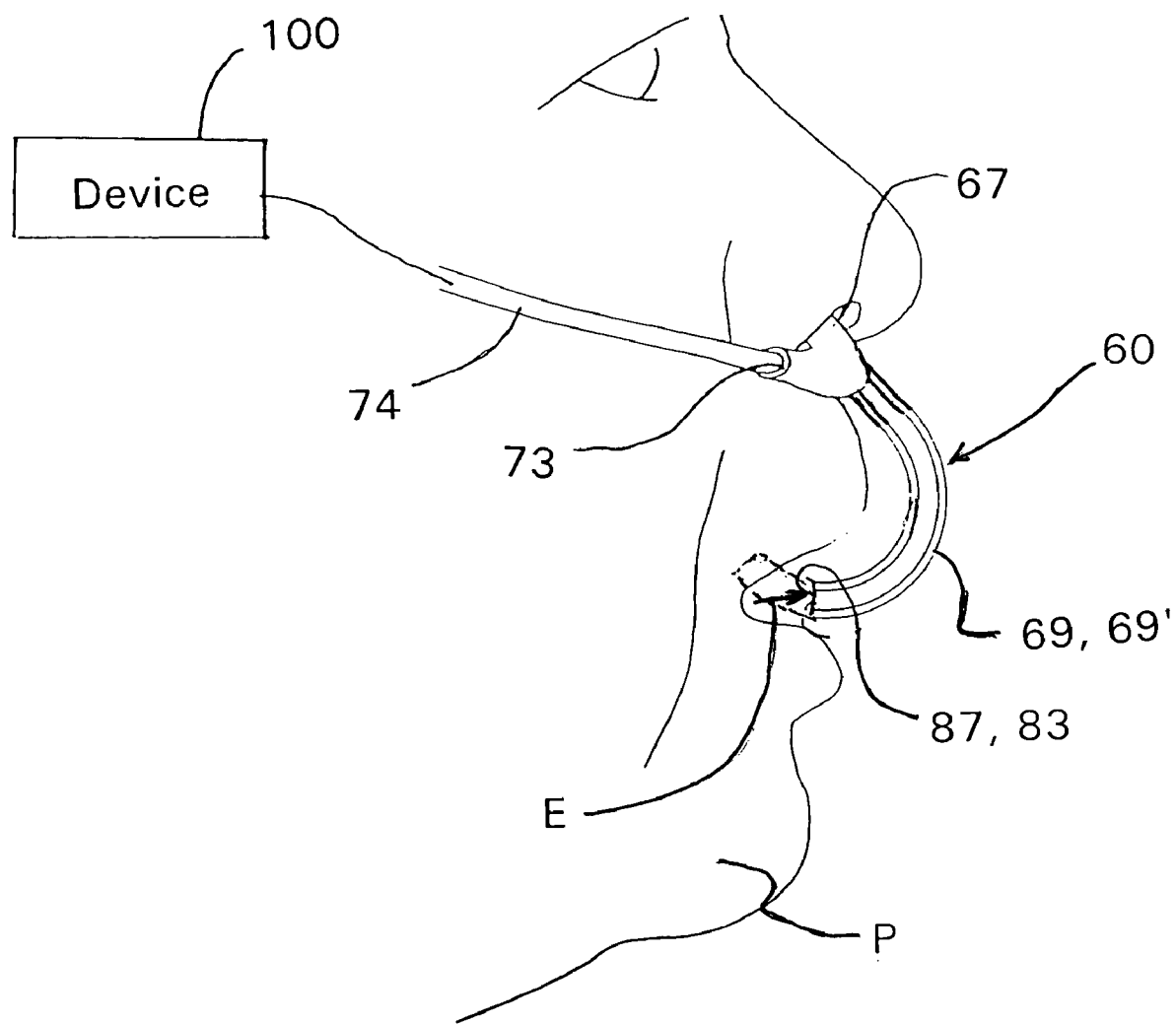
FIG. 12B is a side elevational view showing the trimmed orientation of the mouthpiece, relative to an open mouth of a patient, for aligning an opening of the mouthpiece with the patient's oral inhalation/exhalation path.

FIG. 12A shows a typical orientation of the mouthpieces 69, 69', relative to a patient's mouth in an opened position following installation of the cannula on the patient. As can be readily observed in FIG. 12A, it is possible that the gas passage openings 83 and 87 initially may not be precisely aligned with the exhalation/inhalation path E of the patient, e.g., the plane defined by the gas passage openings 83 and 87 may not extend substantially normal to the exhalation/inhalation path E. The remote free end of the mouthpieces 69, 69' can be cut or trimmed, as necessary (see FIG. 12B in which the removed or trimmed portion of the mouthpieces 69, 69' is shown in dashed lines), so that thereafter the openings to the internal gas passageways 77, 79 of the mouthpieces 69, 69' lies substantially normal to the exhalation/inhalation path E of the patient. Such alignment of the openings 83 and 87 to the internal gas passageways 77, 79 of the mouthpieces 69, 69' assists with better collection of a gas sample(s), more accurate detection of an exhalation pressure, more accurate delivery of a gas(es), more accurate monitoring of the patient's breathing, etc. The above described arrangement permits minor adjustment of the configuration and/or orientation of the mouthpieces 69, 69'.

With reference to FIGS. 13 and 13A, another embodiment of the cannula mandrel assembly will now be discussed. For the sake of clarity, the nare mandrels are not shown attached respectively to the first or the second sections 1A, 1B of the main body forming mandrel 1 in FIG. 13. As this embodiment is similar to the previous embodiments, identical reference numerals will given to identical elements and only the differences between this embodiment and the embodiment of FIGS. 10A-10D, in particular, will be discussed in detail.

The principal difference between this embodiment and the embodiment of FIGS. 10A-10D is that the rectangular sections 21A and 21B are located slightly closer to one another so the first and second prongs 53, 53', when engaged therewith, are mounted in a closer relationship to one another. That is, each rectangular section 21A and 21B is located about 0.0290 inches of so from an end of either the first or the second sections 1A, 1B of the main body forming mandrel 1 and so that adjacent edges of the first or the second sections 1A, 1B are spaced from one another by a distance of about 0.050 inches. This results in the first and second prongs 53, 53', when engaged with the respective rectangular sections 21A, 21B, being spaced or separated from one another by only a distance of about 0.1100 inches or so.

The net result of this modification occurs during the dipping process. That is, during the dipping process, the first and second prongs 53, 53' are located sufficiently closed to one another such that the plastisol at least partially fills the space or gap formed between the first and second prongs 53, 53' and forms an interconnecting web 89 and well as encases and surrounds each one of the first and second prongs 53, 53 to form an integral mouthpiece comprising a pair of joined or interconnected mouthpieces 69, 69' (see FIG. 13A) which move in unison with one another. In all other respect, this embodiment is substantially identical to the embodiment of FIGS. 10A-10D, 11 and 11A.

Figure 14:
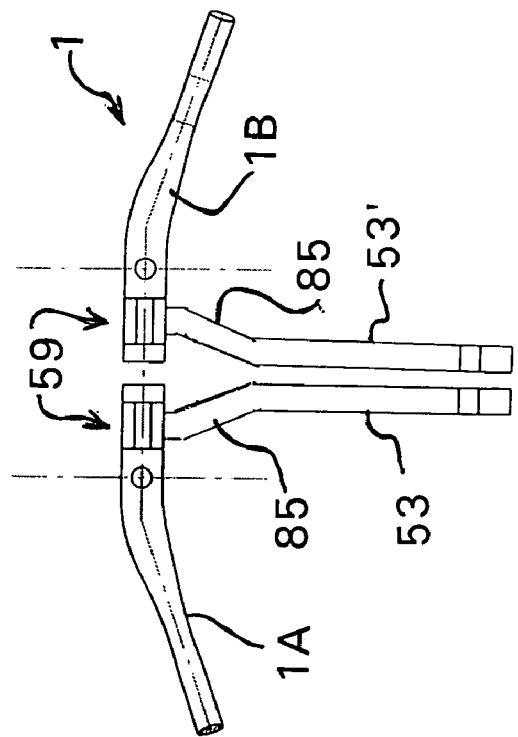
FIG. 14 a front elevational view of still another embodiment showing a partially assembled mandrel assembly having the pair of mouthpiece mandrels assembled with the pair of sections of the main body mandrel.
Figure 14A:
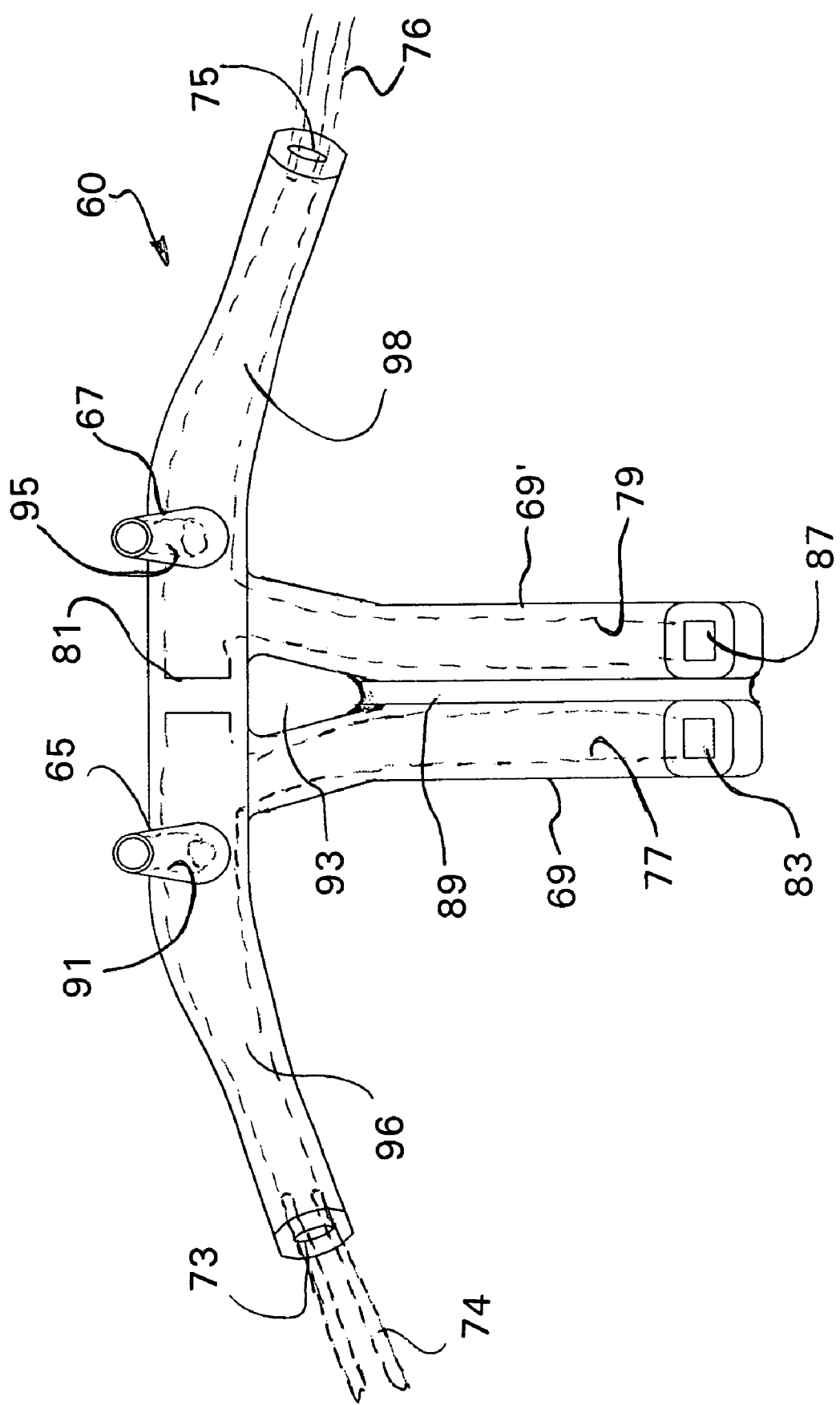
FIG. 14A is a diagrammatic orthogonal view of a cannula, manufactured from the mandrel assembly of FIG. 14, having a pair of separate mouthpieces and two separate flow passageways.

With reference to FIGS. 14 and 14A, another embodiment of the cannula mandrel assembly will now be discussed. For the sake of clarity, the nare mandrels are not shown attached respectively to the first or the second sections 1A, 1B of the main body forming mandrel 1 in FIG. 14. As this embodiment is similar to the previous embodiments, identical reference numerals will given to identical elements and only the differences between this embodiment and the embodiment of FIGS. 10A-10D, in particular, will be discussed in detail.

The principal difference between this embodiment and the embodiment of FIGS. 10A-10D is that each one of the first and second prongs 53, 53' has a small inwardly directed bend or transition 85 formed adjacent the connecting end 59 of the respective first and second prongs 53, 53'. As a result of this small inwardly directed bend or transition 85 toward one another, when the first and second prongs 53, 53' are engaged with the respective first and second sections 1A, 1B, the connecting ends 59 are located further away from one another while the remote free ends of the first and second prongs 53, 53' are located in a closer spaced relationship to one another. That is, the connecting ends 59 of the first and second prongs 53, 53' are spaced from one another by a distance of about ¹⁄₁₆ to ½ inch or while the remote free ends of the first and second prongs 53, 53' are spaced from one another by a distance of about 0.110 inches or so, similar to the embodiment of FIGS. 13 and 13A.

The net result of this modification occurs during the dipping process. That is, during the dipping process, the remote free ends of the first and second prongs 53, 53' are located sufficiently closed to one another such that the plastisol at least partially fills the space or gap between the first and second prongs 53, 53' to form a web 89 therebetween, as well as encases and surrounds each one of the first and second prongs 53, 53 to thereby result in an integral mouthpiece comprising a pair of joined or interconnected mouthpieces 69, 69', once the first and second prongs 53, 53 are removed, which move in unison with one another. In all other respect, this embodiment is substantially identical to the embodiment of FIGS. 10A-10D, 11 and 11A. A through hole 93, which does not contain any plastisol, is formed in the cannula 60 and spaces the web 89 from the main body 71.

Figure 15:
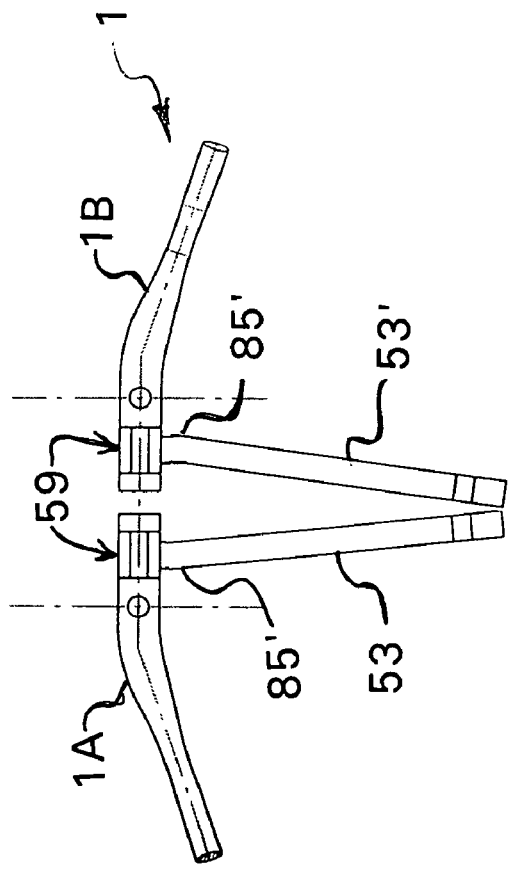
FIG. 15 a front view of yet another embodiment showing a partially assembled mandrel assembly having the pair of mouthpiece mandrels assembled with the pair of sections of the main body mandrel.
Figure 15A:
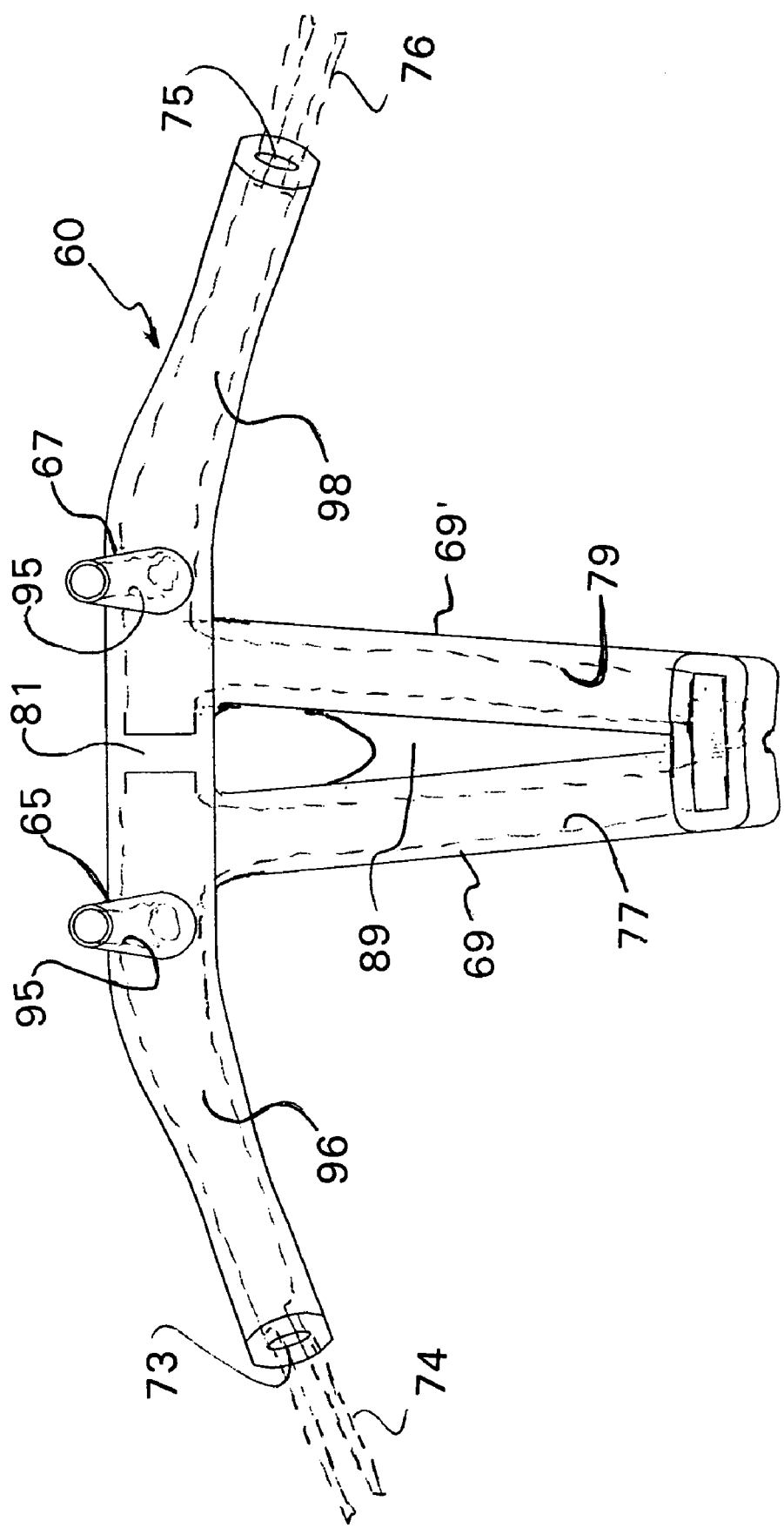
FIG. 15A is a diagrammatic orthogonal view of a cannula, manufactured from the mandrel assembly of FIG. 15, having a pair of separate mouthpieces and two separate flow passageways.

With reference to FIGS. 15 and 15A, a still further embodiment of the cannula mandrel assembly will now be discussed. For the sake of clarity, the nare mandrels are not shown attached respectively to the first or the second sections 1A, 1B of the main body forming mandrel 1 FIG. 15. As this embodiment is similar to the previous embodiments, identical reference numerals will given to identical elements and only the differences between this embodiment and the embodiment of FIGS. 10A-10D, in particular, will be discussed in detail.

The principal difference between this embodiment and the embodiment of FIGS. 10A-10D is that each one of the first and second prongs 53, 53' has a very gradual inclination or taper 85' toward one another, commencing adjacent the connecting end 59 of the respective first and second prongs 53, 53' and extending all the way to the free ends of the first and second prongs 53, 53'. As a result of very gradual inclination or taper toward one another, when the first and second prongs 53, 53' are engaged with the respective first and second sections 1A, 1B, the remote free ends of the first and second prongs 53, 53' are located in very close or possibly in abutting engagement or contact with one another. That is, the remote free ends of the first and second prongs 53, 53' are either in contact with one another or spaced from one another by a distance of less than 0.050 inches or so.

The net result of this modification occurs during the dipping process. That is, during the dipping process, the remote free ends of the first and second prongs 53, 53' are located sufficiently closed to one another such that the plastisol at least partially fills the space or gap between the first and second prongs 53, 53' to form a web 89 therebetween, as well as encases and surrounds each one of the first and second prongs 53, 53 to thereby result in an integral mouthpiece comprising a pair of joined or interconnected mouthpieces 69, 69' which, once the first and second prongs 53, 53 are removed, move in unison with one another. The opening for the two passageways 77, 79 is, in essence, a single common enlarged opening communicating with both passageways 77, 79. A through hole 93, which does not contain any plastisol, is formed in the cannula 60 and spaces the web 89 from the main body 71. In all other respect, this embodiment is substantially identical to the embodiment of FIGS. 10A-10D, 11 and 11A.

According to this application, the term "nasal cannula facepiece" generally comprises: (1) a hollow main body defining an internal chamber therein and having opposed first and second ends; and (2) at least one and preferably first and second nasal prongs which each communicate with the internal chamber of the main body and define respective first and second nasal prong passages.

It is to be appreciated that the mouthpiece could also be injection molded as a single unitary piece or injection molded as two separate pieces, i.e., the facepiece separately molded from the mouthpiece, which are subsequently assembled with one another. Alternatively, the cannula facepiece could also be either injection molded or formed with by polymeric material which is cured. The cannula mouthpiece could be formed by injection molding, by a polymeric material which is cured, or extruded as a separate piece. The facepiece and the mouthpiece are subsequently assembled with one another to form a manufactured cannula.

The cannula, manufactured according to the present invention, is primarily a divided cannula having two completely separate gas flow paths with each completely separate flow path communicating both with the nasal cavity, via one of the patient's nostrils, and the mouth or the oral cavity of the patient. Each one of the mouthpieces, for communicating with the mouth or the oral cavity of the patient, is molded with a sufficient curvature and of a sufficient length such that the free end of both mouthpieces will be typically located closely adjacent, or in direct contact with, the upper lip or lip region of the patient, depending upon the facial contour(s) of the patient. The curvatures of the mouthpieces in combination with the excess length of the mouthpieces results in extra mouthpiece material to facilitate trimming of an excess portion of the free thereof so that the openings, for both mouthpieces, can be aligned substantially normal to the inhalation/exhalation path of the patient and thereby increase the sensitivity of the cannula.

Since certain changes may be made in the above described improved cannula and method of manufacturing the same, without departing from the spirit and scope of the invention herein involved, it is intended that all of the subject matter of the above description or shown in the accompanying drawings shall be interpreted merely as examples illustrating the inventive concept herein and shall not be construed as limiting the invention.

We claim:

1. A single, unitary nasal cannula comprising:
a hollow main body having opposed first and second ends with a first opening formed in the first end and a second opening formed in the second end, and the main body defining an internal chamber therein;
a partition dividing the internal chamber of the hollow main body into completely separate first and second flow compartments, the first flow compartment comprising the first opening and the second flow compartment comprising the second opening;
a flow passageway of a first nasal prong communicating with the first flow compartment of the hollow main body and a flow passageway of a first mouth piece communicating with the first flow compartment of the hollow main body to define a first flow path which communicates with both a first nostril and a mouth of a patient for preforming a first function, the first nasal prong being integrally coupled to the main body and extending from the main body in one direction to facilitate communication between the first nasal prong and the first nostril of the patent, the first mouth piece being integrally coupled to the main body and extending from the main body in another direction to facilitate communication between the first mouth piece and the mouth of the patient;
a flow passageway of a second nasal prong communicating with the second flow compartment of the hollow main body and a flow passageway of a second mouth piece communicating with the second flow compartment to define a second flow path which communicates with both a second nostril and the mouth of the patient for preforming a second function simultaneously during performance of the first function, the second nasal prong being integrally coupled to the main body and extending from the main body in one direction to facilitate communication between the second nasal prong and the second nostril of the patent, the second mouth piece being integrally coupled to the main body and extending from the main body in another direction to facilitate communication between the second mouth piece and the mouth of the patient; wherein the first nasal prong is integrally coupled to the main body at a first location and the first mouth piece is integrally coupled to the main body at a second location such that the flow passageway of the first nasal prong is completely independent of the flow passageway of the first mouth piece; and the second nasal prong is integrally coupled to the main body at a third location, and the second mouth piece is integrally coupled to the main body at a fourth location such that the flow passageway of the second nasal prong is completely independent of the flow passageway of the second mouth piece.

2. The cannula according to claim 1, wherein a first tubing is connected to the first opening in the first end of the cannula for one of supplying a gas thereto, removing a gas therefrom, and measuring air pressure therein and a second tubing is connected to the second opening in the second end of the cannula for one of supplying a gas thereto, removing a gas therefrom and measuring air pressure therein.

3. The cannula according to claim 2, wherein an opposite end of the first tubing is connected to a device for one of supplying a gas thereto, removing a gas sample therefrom and measuring air pressure therein, and an opposite end of the second tubing is connected to a device for one of supplying a gas thereto, removing a gas sample therefrom and measuring air pressure therein.

4. The cannula according to claim 2, wherein the first and second gas passageways have a substantially identical internal cross sectional area to one another.

5. The cannula according to claim 2, wherein the first and second gas passageways have different internal cross sectional area from one another.

6. The cannula according to claim 2, wherein the first gas passageway has a larger internal cross sectional area than an internal cross sectional area of the second gas passageway.

7. The cannula according to claim 2, wherein the first and second mouthpieces extend substantially parallel to but are spaced from one another and a web interconnects the first mouthpiece with the second mouthpiece.

8. The cannula according to claim 1, wherein a first end of a first tubing is connected to the first opening in the first end of the cannula and an opposite end of the first tubing is connected to a device for supplying a treating gas to the first compartment, and a first end of a second tubing is connected to the second opening in the second end of the cannula and an opposite end of the second tubing is connected to a device for facilitating one of monitoring, detecting and sampling of a gas withdrawn from the patient via the second fluid passageway.

9. The cannula according to claim 8, wherein the device for supplying a treating gas to the first compartment is an oxygen supply device, and the device for facilitating one of monitoring, detecting and sampling of a gas withdrawn from the patient via the second fluid passageway is a capnograph.

10. The cannula according to claim 1, wherein the first and second mouthpieces extend substantially parallel to one another but are spaced from one another by a distance of between about ⅛ of an inch to about ½ of an inch.

11. The cannula according to claim 1, wherein the first and second mouthpieces each have a radius of curvature between about 0.5 of an inch to about 2.5 inches.

12. The cannula according to claim 1, wherein the first and second mouthpieces extend substantially parallel to but are spaced from one another and the first and second mouthpieces each have a substantially similar radius of curvature.

13. The cannula according to claim 1, wherein the main body, the first and the second nasal prongs and the first and second mouthpieces are all formed as an integral molded structure during a single manufacturing process.

14. The cannula according to claim 1, wherein the first nasal prong and the first mouth piece extend from the main body in generally opposite directions from each other and the second nasal prong and the second mouth piece extend from the main body in generally opposite directions from each other.

* * * * *